US010835197B2

(12) United States Patent
Goto et al.

(10) Patent No.: US 10,835,197 B2
(45) Date of Patent: Nov. 17, 2020

(54) MEDICAL DIAGNOSTIC-IMAGING APPARATUS AND MEDICAL-INFORMATION MANAGEMENT APPARATUS

(71) Applicant: Toshiba Medical Systems Corporation, Otawara (JP)

(72) Inventors: Takahiro Goto, Utsunomiya (JP); Shinsuke Tsukagoshi, Nasushiobara (JP); Go Mukumoto, Obu (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 322 days.

(21) Appl. No.: 15/589,060

(22) Filed: May 8, 2017

(65) Prior Publication Data

US 2017/0319166 A1 Nov. 9, 2017

(30) Foreign Application Priority Data

May 9, 2016 (JP) .................. 2016-094105
Apr. 27, 2017 (JP) .................. 2017-088345

(51) Int. Cl.
*A61B 6/00* (2006.01)
*A61B 6/03* (2006.01)
*A61B 6/06* (2006.01)

(52) U.S. Cl.
CPC ............ *A61B 6/5294* (2013.01); *A61B 6/032* (2013.01); *A61B 6/465* (2013.01); *A61B 6/488* (2013.01); *A61B 6/5205* (2013.01); *A61B 6/545* (2013.01); *A61B 6/06* (2013.01); *A61B 6/4035* (2013.01); *A61B 6/481* (2013.01); *A61B 6/504* (2013.01)

(58) Field of Classification Search
CPC ......... A61B 6/032; A61B 6/06; A61B 6/4035; A61B 6/465; A61B 6/481; A61B 6/488; A61B 6/504; A61B 6/5205; A61B 6/5294; A61B 6/545
See application file for complete search history.

(56) References Cited

U.S. PATENT DOCUMENTS

2007/0116337 A1* 5/2007 Toth ...................... A61B 6/032
                                                                 382/128
2011/0091008 A1   4/2011 Hirokawa et al.
2015/0119703 A1* 4/2015 Mitchell ............ A61B 6/5294
                                                                 600/425

FOREIGN PATENT DOCUMENTS

JP   2006075512 A  *  3/2006
JP   2007-181623       7/2007
(Continued)

*Primary Examiner* — Chih-Cheng Kao
(74) *Attorney, Agent, or Firm* — Oblon, McClelland, Maier & Neustadt, L.L.P.

(57) ABSTRACT

An X-ray computer tomography (CT) apparatus according to an embodiment includes processing circuitry. The processing circuitry an operation to change information relating to a range of a part that is defined based on a plurality of anatomical landmarks in any one of image data of a subject and image data of a virtual patient image. The processing circuitry performs any one of a first setting processing and a second setting processing, the first setting processing of changing a part of the anatomical landmarks to define the range of the part, the second setting processing of setting, for a part of the anatomical landmarks, a position departed therefrom by a predetermined length in a predetermine direction as an actual anatomical landmark.

20 Claims, 17 Drawing Sheets

(56) References Cited

FOREIGN PATENT DOCUMENTS

| | | |
|---|---|---|
| JP | 2008-12229 | 1/2008 |
| JP | 5455903 | 3/2014 |

\* cited by examiner

FIG.5

| IDENTIFI-CATION CODE | COORDINATES | | |
|---|---|---|---|
| | POSITIONING | SCAN | |
| | | NON-CONTRASTED PHASE | CONTRASTED PHASE |
| C1 | (x1, y1, z1) | (x'1, y'1, z'1) | (x'1, y'1, z'1) |
| C2 | (x2, y2,,z2) | (x'2, y'2, z'2) | (x'2, y'2, z'2) |
| C3 | (x3, y3, z3) | (x'3, y'3, z'3) | (x'3, y'3, z'3) |
| C4 | (x4, y4, z4) | (x'4, y'4, z'4) | (x'4, y'4, z'4) |
| C5 | (x5, y5, z5) | (x'5, y'5, z'5) | (x'5, y'5, z'5) |
| C6 | (x6, y6, z6) | (x'6, y'6, z'6) | (x'6, y'6, z'6) |
| C7 | (x7, y7, z7) | (x'7, y'7, z'7) | (x'7, y'7, z'7) |
| C8 | (x8, y8, z8) | (x'8, y'8, z'8) | (x'8, y'8, z'8) |
| C9 | (x9, y9, z9) | (x'9, y'9, z'9) | (x'9, y'9, z'9) |
| C10 | (x10, y10, z10) | (x'10, y'10, z'10) | (x'10, y'10, z'10) |
| ⋮ | ⋮ | ⋮ | ⋮ |
| C31 | | | (x'31, y'31, z'31) |
| C32 | | | (x'32, y'32, z'32) |
| C33 | | | (x'33, y'33, z'33) |
| C34 | | | (x'34, y'34, z'34) |
| ⋮ | ⋮ | ⋮ | ⋮ |

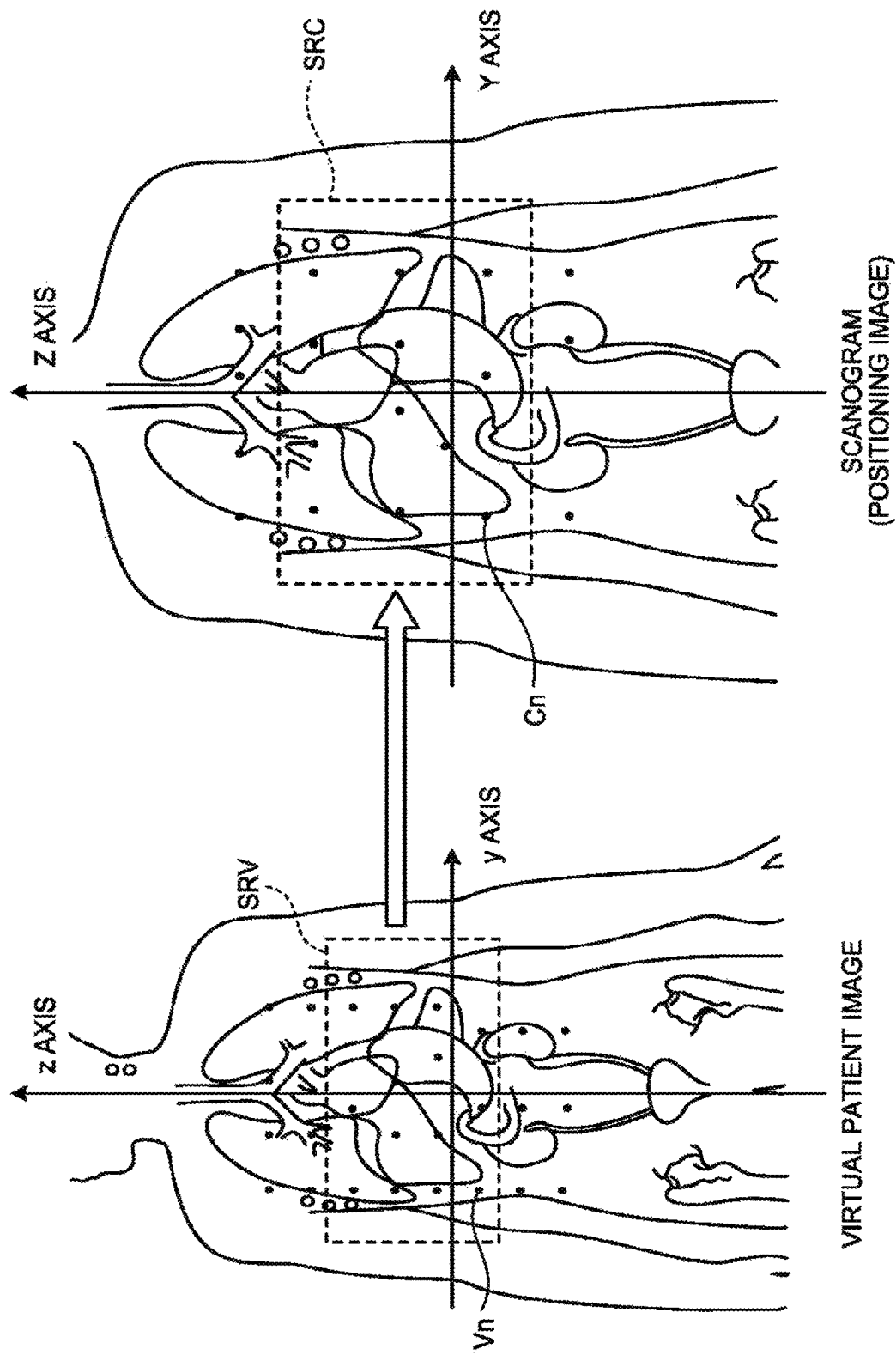

FIG.10

| IMAGING PLAN | IMAGING PART | SCAN START POSITION | SCAN END POSITION |
|---|---|---|---|
| DETAILED EXAMINATION OF LUNG AREA | LUNG | 1 CM ABOVE FLAG POINT AT UPPER END OF RIGHT LUNG | 1 CM BELOW FLAG POINT AT LOWER END OF LEFT LUNG |
| DETAILED EXAMINATION OF COLORECTAL CANCER | LARGE INTESTINE | FLAG POINT AT LIVER UPPER RIM | FLAG POINT AT PUBIS |
| FOLLOW-UP OF BREAST CANCER | HEAD+LUNG | FLAG POINT AT TOP OF HEAD | 1 CM BELOW FLAG POINT AT LOWER END OF LEFT LUNG |
| ⋮ | ⋮ | ⋮ | ⋮ |

FIG.11

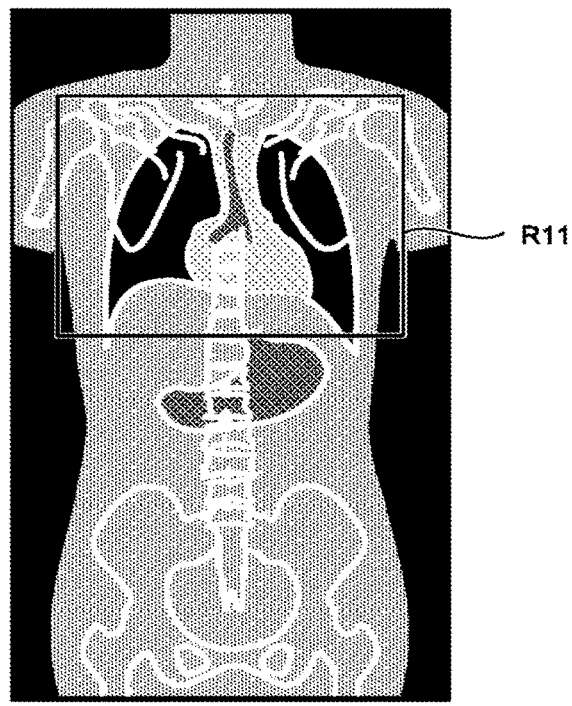

| DATE | PATIENT ID | OPERATION |
|---|---|---|
| 4/3 14:25 | 0101 | SCAN START POSITION IS MOVED 3 CM UPWARD |
| 4/3 16:37 | 0097 | SCAN END POSITION IS MOVED 4 CM DOWNWARD |
| 4/5 12:21 | 0324 | SCAN START POSITION IS MOVED 5 CM UPWARD |
| 4/5 17:05 | 0105 | SCAN START POSITION IS MOVED 4 CM UPWARD |
| ⋮ | ⋮ | ⋮ |

FIG.14

| IMAGING PLAN | IMAGING PART | SCAN START POSITION | SCAN END POSITION |
|---|---|---|---|
| DETAILED EXAMINATION OF LUNG AREA | LUNG | FLAG POINT AT NECK | 1 CM BELOW FLAG POINT AT LOWER END OF LEFT LUNG |
| DETAILED EXAMINATION OF COLORECTAL CANCER | LARGE INTESTINE | FLAG POINT AT LIVER UPPER RIM | FLAG POINT AT PUBIS |
| FOLLOW-UP OF BREAST CANCER | HEAD+LUNG | FLAG POINT AT TOP OF HEAD | 1 CM BELOW FLAG POINT AT LOWER END OF LEFT LUNG |
| ⋮ | ⋮ | ⋮ | ⋮ |

FIG.15

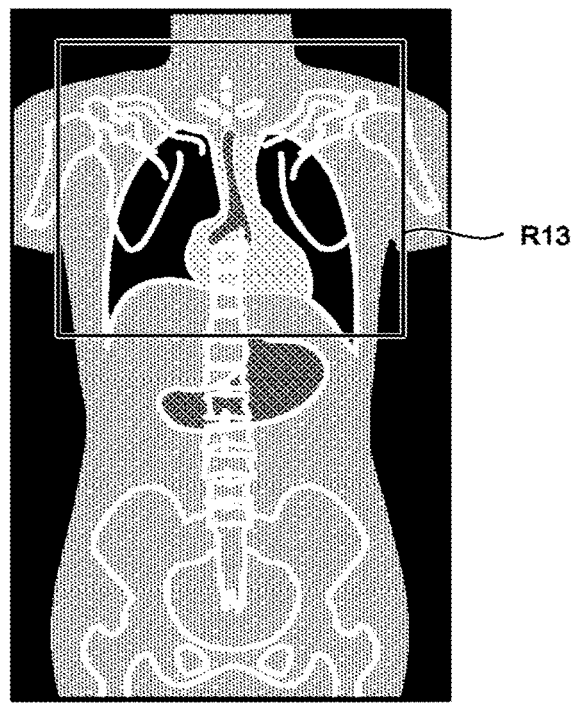

FIG.19

| IMAGING PLAN | IMAGING PART | SCAN START POSITION | SCAN END POSITION |
|---|---|---|---|
| DETAILED EXAMINATION OF LUNG AREA | LUNG | 4 CM ABOVE FLAG POINT AT UPPER END OF RIGHT LUNG | 1 CM BELOW FLAG POINT AT LOWER END OF LEFT LUNG |
| DETAILED EXAMINATION OF COLORECTAL CANCER | LARGE INTESTINE | FLAG POINT AT LIVER UPPER RIM | FLAG POINT AT PUBIS |
| FOLLOW-UP OF BREAST CANCER | HEAD+LUNG | FLAG POINT AT TOP OF HEAD | 1 CM BELOW FLAG POINT AT LOWER END OF LEFT LUNG |
| ⋮ | ⋮ | ⋮ | ⋮ |

FIG.20

| DATE | PATIENT ID | EXAMINATION ORDER | IMAGING PLAN |
|---|---|---|---|
| 4/3 14:25 | 0101 | COLORECTAL CANCER, DETAILED EXAMINATION | DETAILED EXAMINATION OF COLORECTAL CANCER |
| 4/3 16:37 | 0097 | BREAST CANCER, FOLLOW-UP, CONTRASTED SIMPLE IMAGING | FOLLOW-UP OF BREAST CANCER |
| 4/5 12:21 | 0324 | COLORECTAL CANCER, 3D WISHED | DETAILED EXAMINATION OF COLORECTAL CANCER |
| 4/5 17:05 | 0105 | COLORECTAL CANCER, DETAILED EXAMINATION | DETAILED EXAMINATION OF COLORECTAL CANCER |
| ⋮ | ⋮ | ⋮ | ⋮ |

MEDICAL DIAGNOSTIC-IMAGING APPARATUS AND MEDICAL-INFORMATION MANAGEMENT APPARATUS

CROSS-REFERENCE TO RELATED APPLICATIONS

This application is based upon and claims the benefit of priority from Japanese Patent Application No. 2016-094105, filed on May 9, 2016 and Japanese Patent Application No. 2017-088345, filed on Apr. 27, 2017; the entire contents of which are incorporated herein by reference.

FIELD

Embodiments described herein relate generally to a medical diagnostic-imaging apparatus and a medical-information management apparatus.

BACKGROUND

Conventionally, in imaging using an X-ray computed tomography (CT) apparatus, positioning imaging to collect a positioning image (scano-image) is performed before actual imaging. In an X-ray CT apparatus, imaging range setting or input of various kinds of imaging conditions are performed on the positioning image. These operations are manually performed by an operator.

BRIEF DESCRIPTION OF THE DRAWINGS

FIG. 5 is a diagram for explaining one example of the part detection processing performed by the detecting function according to the first embodiment;

FIG. 9 shows a conversion example of a scan range by coordinate transformation according to the first embodiment;

FIG. 10 shows one example of information of a scan range per imaging plan that is stored in the storage according to the first embodiment;

FIG. 11 is a diagram for explaining processing of a storing function according to the first embodiment;

FIG. 14 is a diagram for explaining processing of an updating function according the first embodiment;

FIG. 15 is a diagram for explaining processing of the updating function according to the first embodiment;

FIG. 19 is a diagram for explaining processing of an updating function according to the second embodiment;

FIG. 20 is a diagram for explaining processing by a storing function according to a third embodiment.

DETAILED DESCRIPTION

An X-ray CT apparatus according to an embodiment includes processing circuitry. The processing circuitry accepts an operation to change information relating to a range of a part that is defined based on anatomical landmarks in image data or a subject or image data of a virtual patient image. The processing circuitry performs first setting processing of changing a part of anatomical landmarks to define a range of a part, or second setting processing of setting, for a part of the anatomical landmarks, a position departed therefrom by a predetermined length in a predetermined direction as an actual anatomical landmark, based on the information relating to a range of a part after the change.

Embodiments of the X-ray CT apparatus are explained in detail below referring to the accompanying drawings. In the following, a medical-information processing system including the X-ray CT apparatus is explained as an example. Although only one each of a server device and a terminal device are illustrated in a medical-information processing system 100 shown in FIG. 1, more server devices and terminal devices can be included in an actual state. Moreover, for example, the medical-information processing system 100 can include a medical diagnostic-imaging apparatus, such as an X-ray diagnostic apparatus, a magnetic resonance imaging (MRI) apparatus, and an ultrasonic diagnostic apparatus, also.

(First Embodiment)

Figure 1:
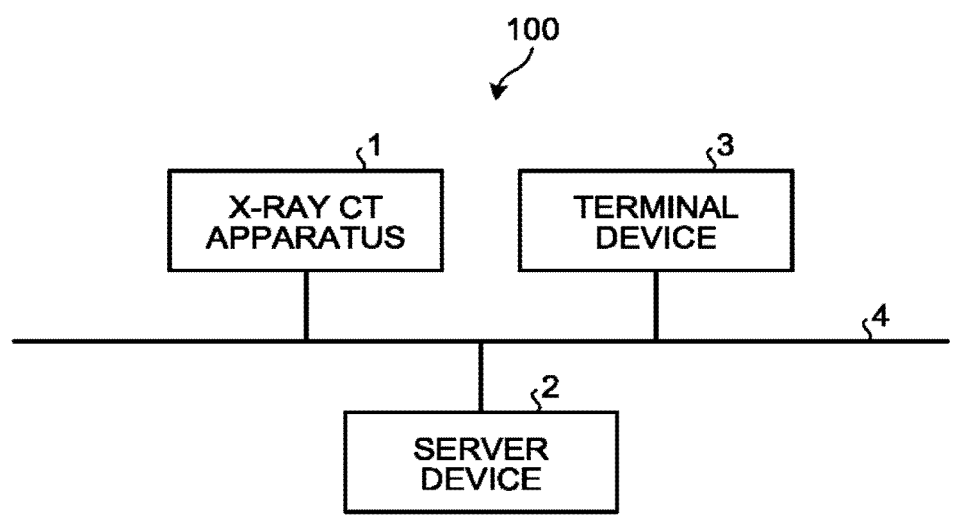
FIG. 1 shows one example of a configuration of a medical-information processing system according to a first embodiment.

FIG. 1 shows one example of a configuration of a medical-information processing system according to a first embodiment. As shown in FIG. 1, the medical-information processing system 100 according to the first embodiment includes an X-ray CT apparatus 1, a server device 2, and a terminal device 3. The X-ray CT apparatus 1, the server device 2, and the terminal device 3 can communicate with each other directly or indirectly through, for example, an in-hospital local area network (LAN) 4 that is installed in a hospital. For example, when a picture archiving and communication system (PACS) is installed in the medical-information processing system 100, the respective devices mutually communicate a medical image and the like conforming to the digital imaging and communications in medicine (DICOM) standard.

Moreover, in the medical-information processing system 100, for example, a hospital information system (HIS), a radiology information system (RIS), or the like is installed, and various kinds of information is managed. For example, the terminal device 3 transmits an examination order that is created according to the system described above to the X-ray CT apparatus 1 or the server device 2. The X-ray CT apparatus 1 acquires patient information from the examination order directly received from the terminal device 3, or from a patient list (modality work list) per modality created by the server device 2 that has received the examination order, and collects X-ray CT-image data per patient. The X-ray CT apparatus 1 transmits the collected X-ray CT-image data or image data that is generated by performing various kinds of image processing on the X-ray CT-image data, to the server device 2. The server device 2 stores the X-ray CT-image data and the image data that are received from the X-ray CT apparatus 1, generates image data from X-ray CT-image data, and transmits, to the terminal device 3, image data according to an acquisition request from the terminal device 3. The terminal device 3 displays the image data received from the server device 2 on a monitor and the like. In the following, the respective devices are explained.

The terminal device 3 is a device that is installed in each department in a hospital, and that is operated by a doctor working in the department, and is a personal computer (PC), a tablet PC, a personal digital assistant (PDA), a mobile phone, or the like. For example, to the terminal device 3, chart information such as a symptom of a patient and findings of a doctor is input by a doctor. Moreover, to the terminal device 3, an examination order to order an examination by the X-ray CT apparatus 1 is input, and transmits the input examination order to the X-ray CT apparatus 1 or the server device 2. That is, a doctor at a hospital department operates the terminal device 3, to read reception information of a patient and information in an electronic chart, examines the patient, and input chart information in the read electronic chart. The doctor at the hospital department then transmits an examination order by operating the terminal device 3, according to necessity of an examination by using the X-ray CT apparatus 1.

The server device 2 is a device that stores a medical image collected by the medical diagnostic-imaging apparatus (for example, X-ray CT-image data collected by the X-ray CT apparatus 1 and image data), or that performs various kinds of image processing on the medical image, and is, for example, a PACS server, or the like. For example, the server device 2 receives examination orders from the terminal device 3 that is installed in each department, generates a patient list per medical diagnostic-imaging apparatus, and transmits the generated patient list to each medical diagnostic-imaging apparatus. As one example, the server device 2 receives an examination order to perform an examination by the X-ray CT apparatus 1 from the terminal device 3 of each department to create a patient list, and transmits the created patient list to the X-ray CT apparatus 1. The server device 2 then stores X-ray CT-image data collected by the X-ray CT apparatus 1 and image data, and transmits the X-ray CT-image data and the image data to the terminal device 3 according to an acquisition request from the terminal device 3.

Figure 2:
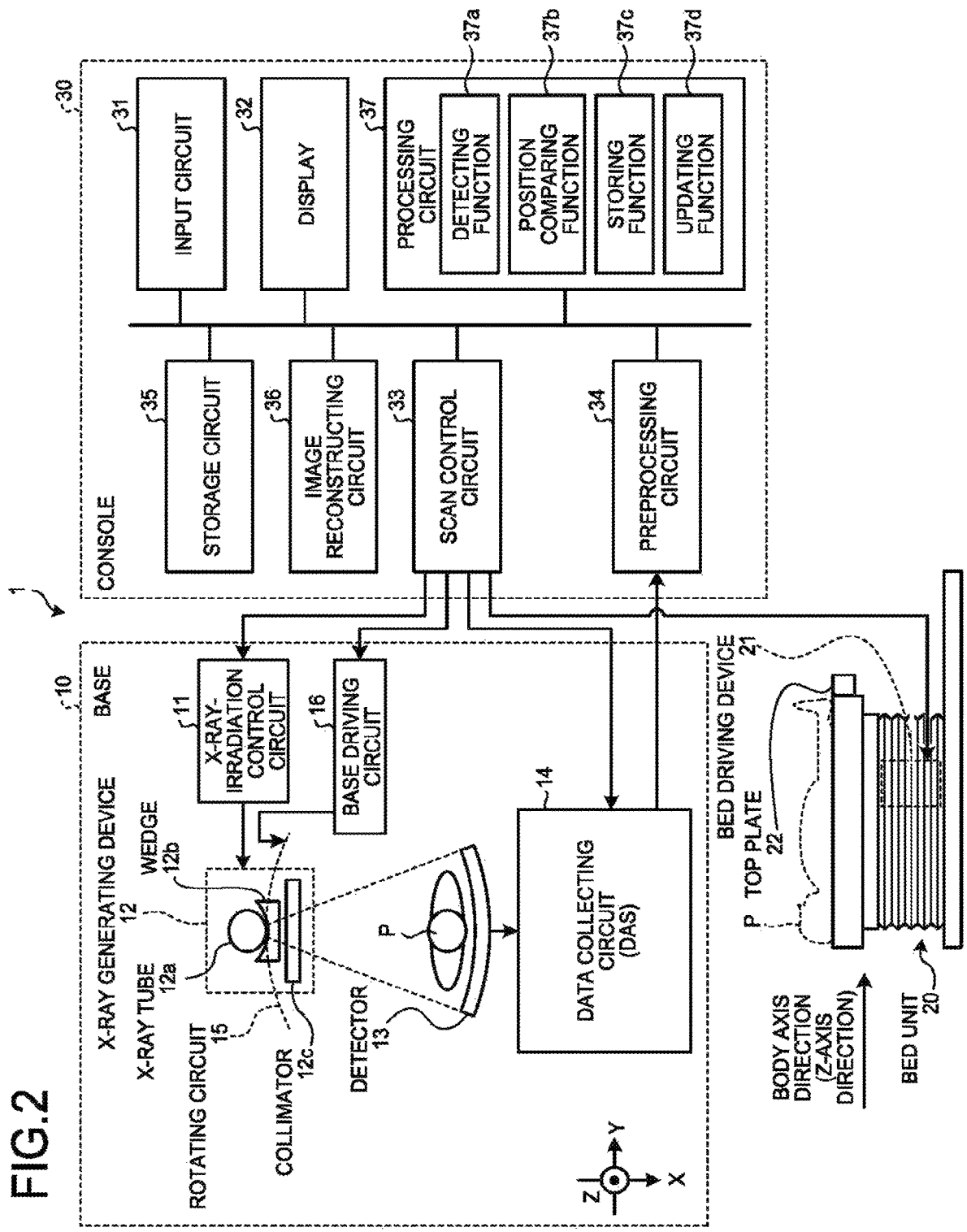
FIG. 2 shows one example of a configuration of an X-ray CT apparatus according to the first embodiment.

The X-ray CT apparatus 1 collects X-ray CT-image data per patient, and transmits the X-ray CT-image data and image data that is generated by performing various kinds of image processing on the X-ray CT-image data to the server device 2. FIG. 2 shows one example of a configuration of the X-ray CT apparatus 1 according to the first embodiment. As shown in FIG. 2, the X-ray CT apparatus 1 according to the first embodiment includes a base 10, a bed unit 20, and a console 30.

The base 10 is a device that irradiates an X-ray to a subject P (patient), and detects an X-ray that has passed through the subject P to output to the console 30, and includes an X-ray-irradiation control circuit 11, an X-ray generating device 12, a detector 13, a data collecting circuit (data acquisition system (DAS)) 14, a rotating frame 15, and a base driving circuit 16.

The rotating frame 15 is a frame that supports the X-ray generating device 12 and the detector 13 so as to oppose to each other about the subject P, and that is formed in an annular shape rotating at high speed in a circular orbit about the subject P in center by the base driving circuit 16 described later.

The X-ray-irradiation control circuit 11 is a device that supplies a high voltage to an X-ray tube 12a as a high-voltage generating unit, and the X-ray tube 12a generates an X-ray by using the high voltage supplied from the X-ray-irradiation control circuit 11. The X-ray-irradiation control circuit 11 adjusts an amount of X-ray to be irradiated to the subject P by adjusting a tube voltage and a tube current to be supplied to the X-ray tube 12a under control of scan control circuitry 33 described later.

Moreover, the X-ray-irradiation control circuit 11 switches a wedge 12b. Furthermore, the X-ray-irradiation control circuit 11 adjusts an irradiation range (a fan angle or a cone angle) of an X-ray by adjusting an opening degree of a collimator 12c. Note that in the present embodiment, it can be arranged such that more than one kind of wedge is manually switched by an operator.

The X-ray generating device 12 is a device that generates an X-ray and irradiates the generated X-ray to the subject P, and includes the X-ray tube 12a, the wedge 12b, and the collimator 12c.

The X-ray tube 12a is a vacuum tube that irradiates an X-ray beam to the subject P by a high voltage supplied from a high-voltage generating unit not shown, and irradiates the X-ray beam onto the subject P with rotation of the rotating frame 15. The X-ray tube 12a generates an X-ray beam that radiates in a fan angle and a cone angle. For example, the X-ray tube 12a can emit an X-ray continuously all around the subject P for full reconstruction, or can emit an X-ray continuously in an irradiation range (180 degrees+fan angle) enabling half reconstruction for the half reconstruction by the control of the X-ray-irradiation control circuit 11. Moreover, the X-ray tube 12a can emit an X-ray intermittently (pulse X-ray) at predetermined positions (tube position) by the control of the X-ray-irradiation control circuit 11. Furthermore, the X-ray-irradiation control circuit 11 can modulate the intensity of an X-ray to be emitted from the X-ray tube 12a also. For example, the X-ray-irradiation control circuit 11 increases the intensity of an X-ray to be emitted from the X-ray tube 12a at a specific tube position, and decreases the intensity of an X-ray to be emitted from the X-ray tube 12a in a range other than the specific tube position.

The wedge 12b is an X-ray filter to adjust an amount of an X-ray that is emitted from the X-ray tube 12a. Specifically, the wedge 12b is a filter through which an X-ray irradiated from the X-ray tube 12a passes to be attenuated so that the X-ray to be irradiated to the subject P from the X-ray tube 12a has a predetermined distribution. For example, the wedge 12b is a filter that is obtained by processing aluminum to have a predetermined target angle and a predetermined thickness. The wedge is called wedge filter, or bow-tie filter.

The collimator 12c is a slit to narrow an irradiation range of an X-ray, the amount of which has been adjusted by the wedge 12b, by the control of the X-ray-irradiation control circuit 11 described later.

The base driving circuit 16 rotates the X-ray generating device 12 and the detector 13 on a circular orbit about the subject P in center, by driving the rotating frame 15 to be rotated.

The detector 13 is a two-dimensional array detector (surface detector) that detects an X-ray that has passed through the subject P, and has rows of detecting devices in which X-ray detectors for multiple channels are arranged are aligned in multiple rows along a body axis direction (a Z-axis direction shown in FIG. 2) of the subject P. Specifically, the detector 13 according to the first embodiment has X-ray detecting devices that are arranged in multiple rows of 320 rows and the like along the body axis direction of the subject P, and is capable of, for example, detecting an X-ray that has passed through the subject P in a wide range, such as a range including a lung and a heart of the subject P.

The data collecting circuit 14 is a DAS, and collects projection data from detection data of an X-ray detected by the detector 13. For example, the data collecting circuit 14 performs amplification processing, analog-to-digital (A/D) conversion processing, sensitivity correction processing among channels, and the like on an X-ray-intensity distribution data that is detected by the detector 13, to generate projection data, and transmits the generated projection data to the console 30 described later. For example, when an X-ray is continuously emitted from the X-ray tube 12a while the rotating frame 15 is rotating, the data collecting circuit 14 collects a projection data group corresponding to all circumference (360 degrees). Moreover, the data collecting circuit 14 transmits the respective collected projection data associating with a tube position, to the console 30 described later. The tube position is information indicating a projection direction of the projection data. Note that the sensitivity correction processing among channels can be performed by preprocessing circuitry 34 described later.

The bed unit 20 is a device on which the subject P is placed, and as shown in FIG. 2, includes a bed driving device 21, and a top plate 22. The bed driving device 21 moves the top plate 22 in the Z-axis direction, and moves the subject P to the inside of the rotating frame 15. The top plate 22 is a plate on which the subject P is placed.

The base 10 rotates the rotating frame 15 while moving the top plate 22, for example, and performs helical scanning in which the subject P is scanned helically. Alternatively, the base 10 performs conventional scanning in which the subject P is scanned in a circular orbit by rotating the rotating frame 15 while the position of the subject P is fixed after the top plate 22 is moved. Alternatively, the base 10 performs step-and-shoot in which the conventional scanning is performed in more than one scanning area while changing the position of the top plate 22 at regular intervals.

The console 30 is a device that accepts an operation of the X-ray CT apparatus 1 by an operator, and that reconstructs X-ray-CT image data by using projection data collected by the base 10. The console 30 includes, as shown in FIG. 2, an input circuit 31, a display 32, the scan control circuitry 33, the preprocessing circuitry 34, storage 35, image reconstructing circuitry 36, and processing circuitry 37.

The input circuit 31 has a mouse, a keyboard, a trackball, a switch, a button, a joystick, and the like used by an operator of the X-ray CT apparatus 1 to input various kinds of instructions and settings, and transfers information about the instructions and settings accepted from the operator to the processing circuitry 37. For example, the input circuit 31 accepts an imaging condition of X-ray-CT image data, a reconstruction condition at the time of reconstructing X-ray-CT image data, an image processing condition for X-ray-CT image data, and the like from the operator. Moreover, the input circuit 31 accepts a specification operation to specify a portion on an image.

The display 32 is a monitor that is referred to by an operator, and displays image data that is generated from X-ray-CT image data to an operator, or displays a graphical user interface (GUI) to accept various kinds of instructions and settings and the like from the operator through the input circuit 31 under control of the processing circuitry 37. Moreover, the display 32 displays a plan screen of a scanning plan, a screen during scanning, and the like. Furthermore, the display 32 displays a virtual patient image including exposure information, image data, and the like. The virtual patient image displayed by the display 32 is described in detail later.

The scan control circuitry 33 controls collection processing of projection data in the base 10 by controlling operation of the X-ray-irradiation control circuit 11, the base driving circuit 16, the data collecting circuit 14, and the bed driving device 21, under control of the processing circuitry 37. Specifically, the scan control circuitry 33 controls positioning imaging to collect a positioning image (scano-image), and collection processing of projection data in actual imaging (actual scanning) to collect an image to be used for diagnosis. The X-ray CT apparatus 1 according to the first embodiment can image a two-dimensional scano-image and a three-dimensional scano-image.

For example, the scan control circuitry 33 images a two-dimensional scano-image by performing continuous imaging with the X-ray tube 12a fixed at a position of 0 degree (position in a front direction for a subject) while moving the top plate at a constant speed. Alternatively, the scan control circuitry 33 images a two-dimensional scano-image by repeating intermittent imaging synchronized with movement of the top plate, with the X-ray tube 12a fixed at the position of 0 degree, while moving the top plate intermittently. The scan control circuitry 33 can image a positioning image not only from the front direction for the subject, but also from any direction (for example, a side direction, and the like).

Figure 3:
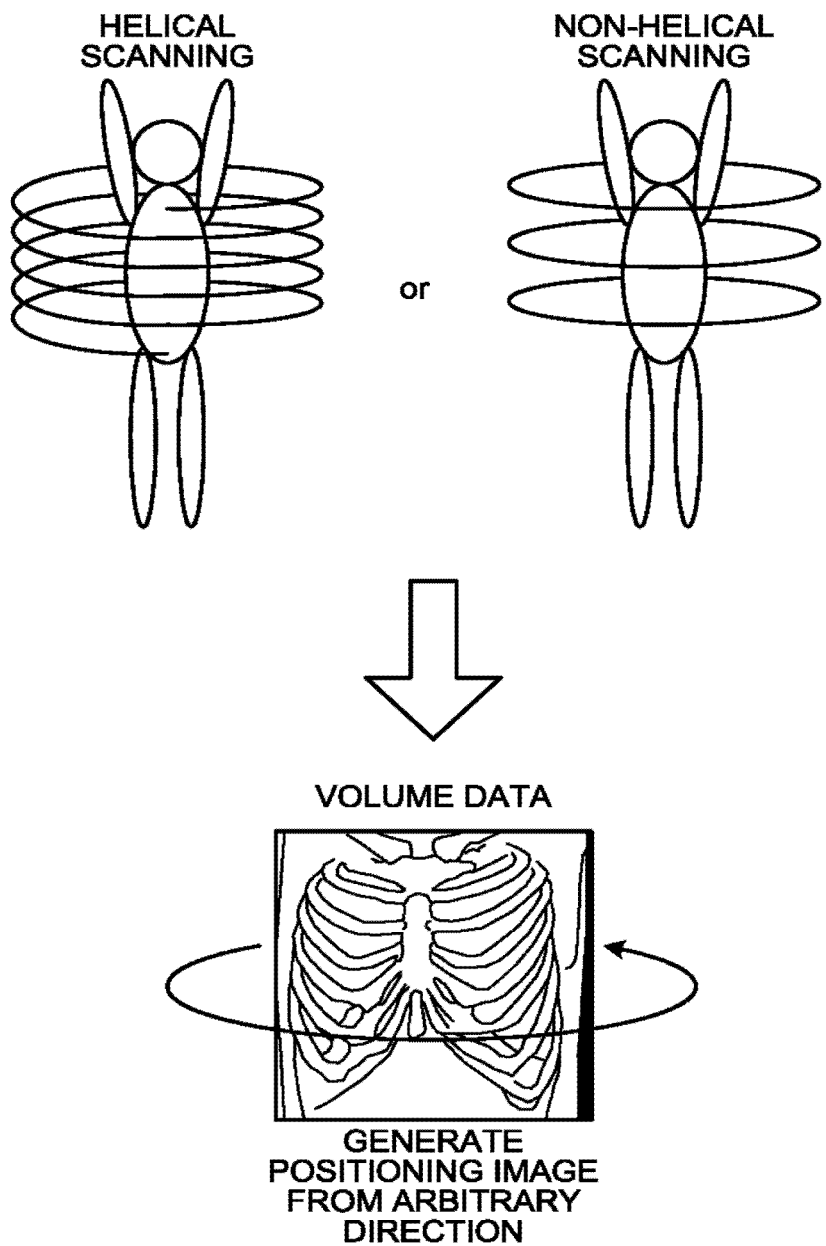
FIG. 3 is a diagram for explaining imaging of a three-dimensional scano-image by scan control circuitry according to the first embodiment.

Moreover, the scan control circuitry 33 acquires a three-dimensional scano-image by collecting projection data of an entire circumference of a subject in scano-image imaging. FIG. 3 is a diagram for explaining imaging of a three-dimensional scano-image by the scan control circuitry 33 according to the first embodiment. For example, the scan control circuitry 33 collects projection data of an entire circumference of a subject by performing helical scanning or non-helical scanning as shown in FIG. 3. The scan control circuitry 33 performs the helical scanning or the non-helical scanning in a wide range, such as an entire chest, an entire abdomen, an entire upper-body, and an entire body of a subject, with a low dose compared to that in actual imaging. As the non-helical scanning, for example, the step-and-shoot scanning described above is performed.

As described by collecting projection data of an entire circumference of a subject by the scan control circuitry 33, the image reconstructing circuitry 36 described later can reconstruct three-dimensional X-ray-CT image data (volume data), and can generate a positioning image from any direction by using the reconstructed volume data as shown in FIG. 3. Whether to image a positioning image in two dimension or in three dimension can be set arbitrarily by an operator, or can be set in advance according to an examination.

Referring back to FIG. 2, the preprocessing circuitry 34 performs correction processing, such as logarithmic conversion processing, offset correction, sensitivity correction, and beam hardening correction, on the projection data generated by the data collecting circuit 14, to generate corrected projection data. Specifically, the preprocessing circuitry 34 generates corrected projection data for each of the projection data of the positioning image that is generated by the data collecting circuit 14 and projection data that is collected in the actual imaging, to store in the storage 35.

The storage 35 stores the projection data generated by the preprocessing circuitry 34. Specifically, the storage 35 stores the projection data of a positioning image, and the projection data for diagnosis collected in the actual imaging, generated by the preprocessing circuitry 34. Moreover, the storage 35 stores image data or a virtual patient image that are generated by the image reconstructing circuitry 36 described later. Furthermore, the storage 35 stores, as necessary, a processing result by the processing circuitry 37 described later. The virtual patient image and the processing result by the processing circuitry 37 are described later.

The image reconstructing circuitry 36 reconstructs X-ray-CT image data by using the projection data stored in the storage 35. Specifically, the image reconstructing circuitry 36 reconstructs X-ray-CT image data from each of the projection data of the positioning image and the projection data of an image used for diagnosis. Various methods are available as a reconstruction method, and the back projection processing is one, for example. Moreover, as the back projection processing, for example, back projection processing by filtered back projection (FBP) can be applied. Alternatively, the image reconstructing circuitry 36 can reconstruct X-ray-CT image data by using a method of successive approximation. The image reconstructing circuitry 36 is one example of an image reconstructing unit.

Furthermore, the image reconstructing circuitry 36 generates various image data by performing various kinds of image processing on X-ray-CT image data. The image reconstructing circuitry 36 stores the reconstructed X-ray-CT image data, and the image data that is generated by various kinds of image processing in the storage 35.

The processing circuitry 37 performs overall control of the X-ray CT apparatus 1 by controlling operation of the base 10, the bed unit 20, and the console 30. Specifically, the processing circuitry 37 controls CT scanning performed in the base 10 by controlling the scan control circuitry 33. Moreover, the processing circuitry 37 controls the image reconstruction processing and the image generation processing in the console 30 by controlling the image reconstructing circuitry 36. Furthermore, the processing circuitry 37 controls to display various kinds of image data stored in the storage 35 on the display 32.

Moreover, the processing circuitry 37 performs a detecting function 37a, a position comparing function 37b, a storing function 37c, and an updating function 37d as shown in FIG. 2. For example, the respective processing functions executed by the detecting function 37a, the position comparing function 37b, the storing function 37c, and the updating function 37d that are components of the processing circuitry 37 shown in FIG. 2 are recorded in the storage 35 in a form of computer-executable program. The processing circuitry 37 is a processor that implements functions corresponding to respective programs by reading and executing the programs from the storage 35. In other words, the processing circuitry 37 that has read the respective programs is to have the respective functions shown in the processing circuitry 37 in FIG. 2. The processing circuitry 37 is one example of a control unit. Moreover, the detecting function 37a is one example of a detecting unit.

The detecting function 37a detects parts of a subject that are included in three-dimensional image data. Specifically, the detecting function 37a detects a part such as an organ that is included in three-dimensional X-ray-CT data (volume data) reconstructed by the image reconstructing circuitry 36. For example, the detecting function 37a detects a part such as an organ based on an anatomical landmark for at least one of volume data of a positioning image and volume data of an image to be used for diagnosis. The anatomical landmark is a point that shows a feature of a specific part such as a bone, an organ, a blood vessel, a nerve, and a lumen. That is, the detecting function 37a detects a bone, an organ, a blood vessel, a nerve, a lumen, and the like included in volume data by detecting a specific anatomical landmark of an organ, a bone, or the like. Moreover, the detecting function 37a can detect a position of a head, a neck, a chest, an abdomen, a leg, and the like included in volume data by detecting a characteristic landmark of a human body. Note that a part explained in the present embodiment indicates a position of the part in addition to the part itself, such as a bone, an organ, a blood vessel, a nerve, and a lumen. In the following, one example of detection of a part performed by the detecting function 37a is explained.

For example, the detecting function 37a extracts, from volume data of a positioning image or volume data of an image to be used for diagnosis, an anatomical landmark based on voxel values included in the volume data. A detecting function 61 compares a position of the anatomical landmark extracted from the volume data with a three-dimensional position of an anatomical landmark in information from a textbook or the like, and removes an incorrect landmark from among the landmarks extracted from the volume data, to optimize the position of the landmark extracted from the volume data. Thus, the detecting function 61 detects each part of the subject included in the volume data. As one example, the detecting function 37a first uses a supervised machine-learning algorithm to extract an anatomical landmark included in the volume data. The supervised machine-learning algorithm described above is created using multiple supervisory images in which correct anatomical landmarks are manually positioned and, for example, decision forest and the like are used.

The detecting function 37a then compares the extracted landmark with a model that indicates a three-dimensional positional relation of an anatomical landmark in a body to optimize the extracted landmark. The model described above is created using the supervisory images described above and, for example, a point distribution model and the like are used. That is, the detecting function 37a compares the extracted landmark with a model in which a shape, a positional relationship, a part-specific point, and the like of a part, are defined based on the supervisory images in which correct anatomical landmarks are manually arranged, and removes an incorrect landmark therefrom to optimize the landmark.

Figure 4A:
FIGS. 4A and 4B are diagrams for explaining one example of part detection processing performed by a detecting function according to the first embodiment.
Figure 4B:
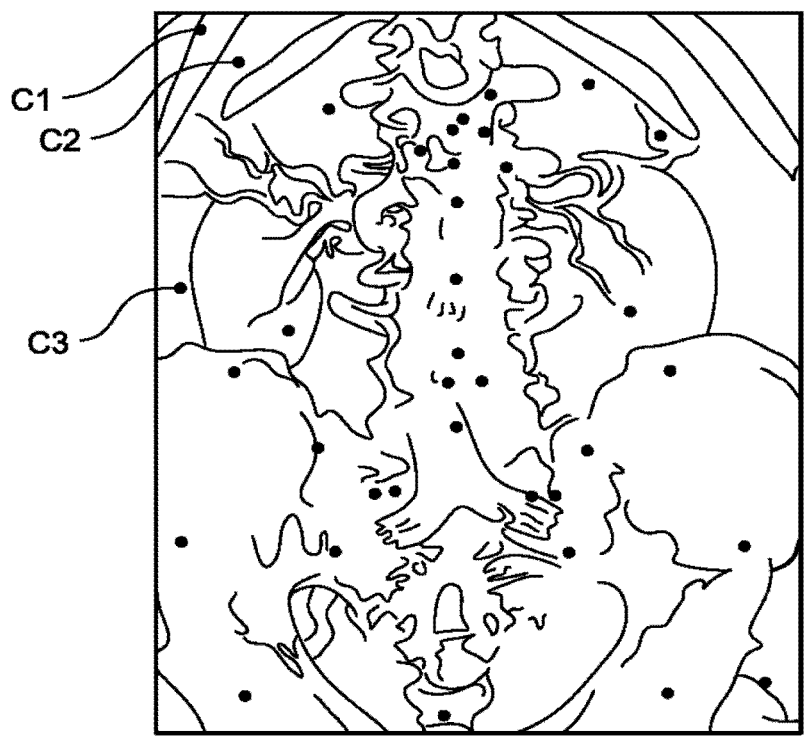

In the following, one example of part detection processing by the detecting function 37a is explained using FIGS. 4A, 4B, 5, and 6. FIGS. 4A, 4B, 5, and 6 are diagrams for explaining one example of the part detection processing performed by the detecting function 37a according to the first embodiment. In FIGS. 4A and 4B, landmarks are arranged two-dimensionally, although the landmarks are arranged three-dimensionally in the actual state. For example, the detecting function 37a applies the supervised machine-learning algorithm to volume data, thereby extracting voxels that are regarded as an anatomical landmark as shown in FIG. 4A (black points in the figure). The detecting function 37a then fits positions of the extracted voxels to a model in which a shape, a positional relationship, a part-specific point, and the like of the part are defined, and removes incorrect landmarks from the extracted voxels, thereby extracting voxels that correspond to more accurate landmarks only.

The detecting function 37a assigns an identification code to identify a landmark that indicates a characteristic of each part, to the extracted landmark (voxel), accompanies information in which the identification code and a position (coordinates) information of each landmark are associated with each other to image data to store in the storage 35. For example, the detecting function 37a assigns an identification code, such as C1, C2, and C3, to the extracted landmark (voxel) as shown in FIG. 4B. The detecting function 61 assigns the identification code per data subjected to the detection processing, to store in the storage 35. Specifically, the detecting function 61 detects a part of a subject included in volume data that has been reconstructed from at least one projection data out of projection data of a positioning image, projection data collected without a contrast agent, and projection data collected in contrast imaging using a contrast agent.

For example, the detecting function 37a accompanies information in which an identification code is associated with coordinates of each voxel (positioning in the figure) detected from volume data of a positioning image, to volume data to store in the storage 35 as shown in FIG. 5. As one example, the detecting function 37a extracts coordinates of a flag point from the volume data of a positioning image, and as shown in FIG. 5, associates "identification code: C1, coordinates $(x_1, y_1, z_1)$", "identification code: C2, coordinates $(x_2, y_2, z_2)$", or the like with the volume data to store it. Thus, the detecting function 37a can find what landmark is at which position in the volume data of a positioning image, and can detect each position of an organ or the like based on the information.

Moreover, the detecting function 61 accompanies information in which an identification code is associated with coordinates of each voxel (scan in the figure) detected from volume data of an image for diagnosis, to volume data to store in the storage 35 as shown in FIG. 5. The detecting function 61 can extract, in scan, coordinates of a flag point from each of the volume data (phase in the figure) contrasted by a contrast agent and the volume data (non-contrasted phase in the figure) that is not contrasted by a contrast agent, and as shown in FIG. 5, and can associate the identification code with the extracted coordinates.

As one example, the detecting function 61 extracts coordinates of a flag point from the volume data of non-contrasted phase, out of the volume data of an image for diagnosis, and as shown in FIG. 5, associates "identification code: C1, coordinates $(x'_1, y'_1, z'_1)$", "identification code: C2, coordinates $(x'_2, y'_2, z'_2)$", or the like with the volume data to store it. Moreover, the detecting function 61 extracts coordinates of a flag point from the volume data of contrasted phase out of the volume data of an image for diagnosis, and as shown in FIG. 5, associates "identification code: C1, coordinates $(x'_1, y'_1, z'_1)$" "identification code: C2, coordinates $(x'_2, y'_2, z'_2)$", or the like with the volume data to store it. When the flag point is extracted from the volume data of contrasted phase, as it is contrasted, the extractable flag point is included. For example, when extracting a flag point from the volume data of contrasted phase, the detecting function 61 can extract a blood vessel that is contrasted by a contrast agent. Therefore, for volume data of contrasted phase, the detecting function 61 associates coordinates $(x'_{31}, y'_{31}, z'_{31})$ to coordinates $(x'_{34}, y'_{34}, z'_{34})$ and the like of flag points such as blood vessels extracted by contrasting it with identification codes C31, C32, C33, and C34, and the like to identify the respective blood vessels as shown in FIG. 6.

As described above, the detecting function 61 can identify a flag point and a position thereof in volume data of a positioning image or an image for diagnosis, and can detect each part such as an organ based on the information. For example, the detecting function 37a detects a position of a subject part, by using information of anatomical positional relationship between a subject part to be a subject of detection and a part around the subject part. As one example, when the subject part is "lung", the detecting function 37a acquires coordinate information that is associated with an identification code indicating characteristics of a lung, and also acquires coordinate information associated with identification codes indicating parts around "lung", such as "rib", "clavicle", "heart", and "diaphragm". The detecting function 37a then acquires a region of "lung" in the volume data by using information of anatomical positional relationship between "lung" and a part therearound, and the acquired coordinate information.

Figure 6:
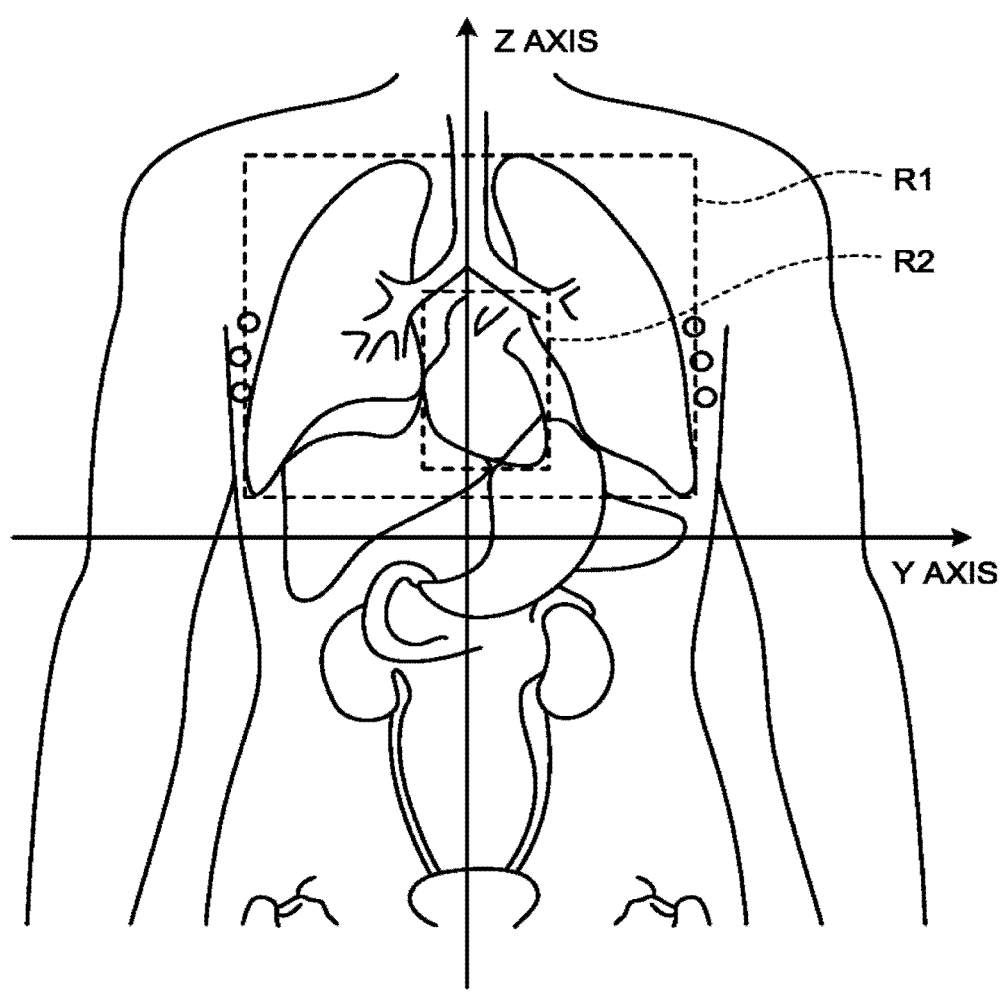
FIG. 6 is a diagram for explaining one example of the part detection processing performed by the detecting function according to the first embodiment.

For example, the detecting function 37a extracts a region R1 corresponding to "lung" in the volume data as shown in FIG. 6 based on the information of positional relationship indicating "lung apex: 2 centimeters (cm) to 3 cm above clavicle", "lower end of lung height of the seventh rib", and the like, and on the coordinate information of the respective part. That is, the detecting function 37a extracts coordinate information of voxels of the region R1 in the volume data. The detecting function 37a accompanies the extracted coordinate information to the volume data, associating with the part information to store it. Similarly, the detecting function 37a can extract a region R2 corresponding to "heart" in the volume data as shown in FIG. 6.

Furthermore, the detecting function 37a extracts a position included in the volume data based on landmarks that define positions of a head, a chest, and the like in a human body. The positions of a head, a chest, and the like in a human body can be defined arbitrarily. For example, if a portion from the seventh cervical vertebra to a lower end of a lung is defined as a chest, the detecting function 37a detects a portion from a landmark corresponding to the seventh cervical vertebra to a landmark corresponding to a lower end of a lung, as a chest. The detecting function 37a can detect a part by various methods other than the method using anatomical landmarks described above. For example, the detecting function 37a can detect a part included in volume data by an area expansion method based on voxel values, and the like.

The position comparing function 37b checks positions of parts in a subject included in three-dimensional image data against positions of respective parts in a human body included in virtual patient data. The virtual patient data is information indicating standard positions of respective parts in a human body. That is, the position comparing function 37b compares a position of a part of a subject with a standard position of the part, and stores a comparison result in the storage 35. For example, the position comparing function 37b performs matching of the virtual patient image in which parts of a human body are arranged at standard positions, and volume data of a subject.

First, the virtual patient image is explained. The virtual patient images are created in advance as images that have been obtained by actually radiographing human bodies that have a standard physique according to respective combinations of parameters relating to body size such as age, adult/infant, male/female, weight, and height, and is stored in the storage 35. That is, the storage 35 stores data of multiple virtual patient images according to combinations of parameters described above. With the virtual patient image stored in the storage 35, an anatomical landmark (landmark) is associated to be stored. For example, in a human body, there are many anatomical landmarks that can be extracted relatively easily from an image based on the structural characteristics and the like by image processing such as pattern recognition. The positions and arrangements of these many anatomical landmarks in a body are roughly determined according to the age, adult/infant, male/female, the weight, the height, and the like.

Figure 7:
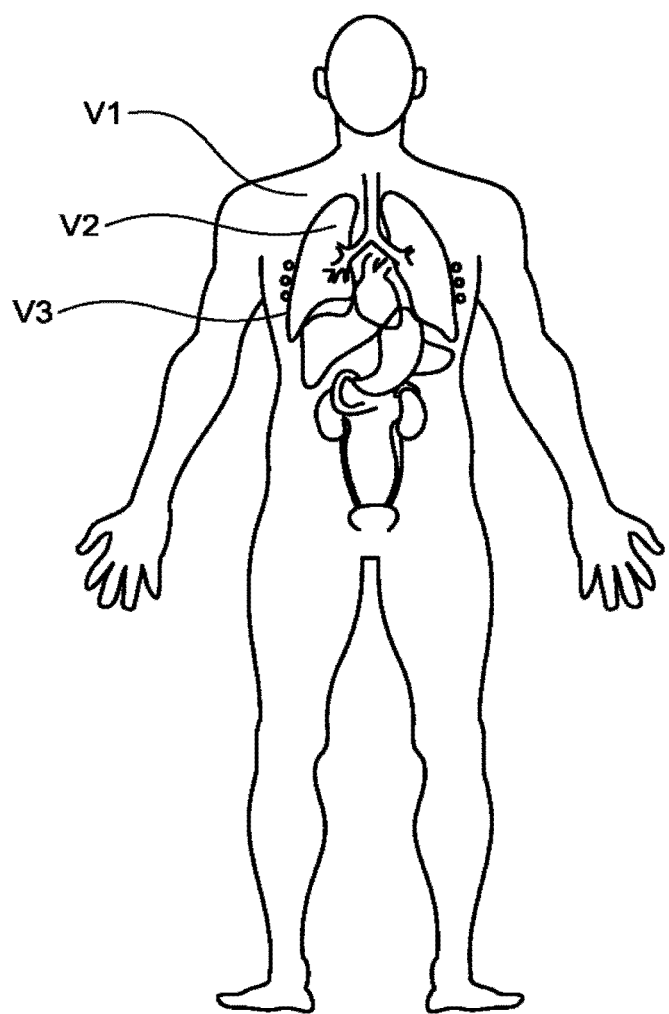
FIG. 7 shows one example of a virtual patient image that is stored by storage according to the first embodiment.

For the virtual patient image stored in the storage 35, these many anatomical landmarks are detected in advance, and position data of the detected landmarks is associated with or accompanied to data of the virtual patient image together with the identification codes of the respective landmarks to be stored. FIG. 7 shows one example of the virtual patient image that is stored by the storage 35 according to the first embodiment. For example, the storage 35 stores a virtual patient image to which anatomical landmarks and identification codes "V1", "V2", and "V3" to identify the landmarks, and the like are associated with a three-dimensional human body that includes a part such as an organ as shown in FIG. 7.

That is, the storage 35 stores coordinates of a landmark in a coordinate space in a three-dimensional image of a human body and an identification code corresponding thereto, associating with each other. As one example, associating with the identification code "V1" shown in FIG. 7, the storage 35 stores coordinates of a corresponding landmark. Similarly, the storage 35 stores an identification code and coordinates of a landmark, associating with each other. Although only a lung, a heart, a liver, a stomach, a kidney, and the like are shown in FIG. 7, a virtual patient image in an actual state includes more organs, such as a bone, a blood vessel, and a nerve. Moreover, although only landmarks corresponding to the identification codes "V1", "V2", and "V3" are shown in FIG. 7, more landmarks are included in an actual case.

Figure 8:
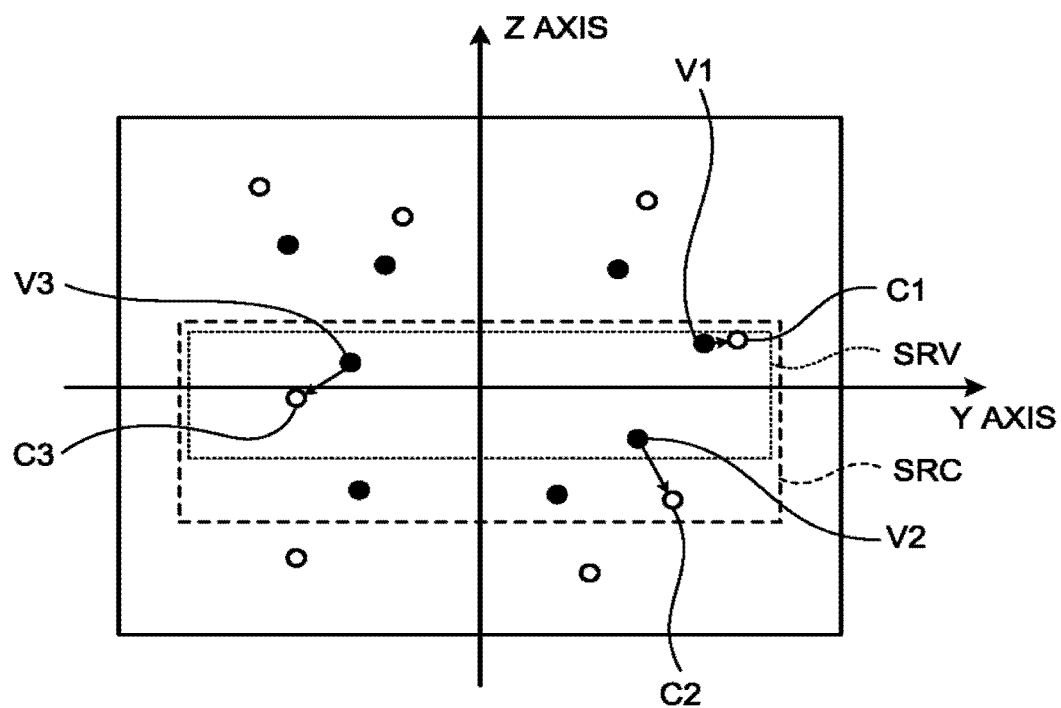
FIG. 8 is a diagram for explaining one example of comparison processing performed by position comparing function according to the first embodiment.

The position comparing function 37b performs matching of a landmark in volume data of a subject detected by the detecting function 37a and a landmark in a virtual patient image described above by using an identification code, to associate a coordinate space of the volume data and a coordinate space of the virtual patient image. FIG. 8 is a diagram for explaining one example of comparison processing performed by the position comparing function 37b according to the first embodiment. FIG. 8 shows a case of performing matching by using three sets landmarks to which identification codes indicating the same landmark are assigned among landmarks detected from a scano-image and landmarks detected from a virtual patient image. However, embodiments are not limited thereto, and matching can be performed by using arbitrary sets of landmarks.

For example, as shown in FIG. 8, when matching landmarks indicated by the identification codes "V1", "V2", and "V3" in a virtual patient image with landmarks indicated by the identification codes "C1", "C2", and "C3" in a scano-image, the position comparing function 37b performs coordinate transformation to minimize a positional difference between the same landmarks, thereby associating coordinate spaces of the images. For example, as shown in FIG. 8, the position comparing function 37b acquires a coordinate transformation matrix "H" below, so as to minimize a total "LS" of positional differences between anatomically same landmarks "V1 (x1, y1, z1), C1 (X1, Y1, Z1)", "V2 (x2, y2, z2), C2 (X2, Y2, Z2)", and "V3 (x3, y3, z3), C3 (X3, Y3, Z3)".

$$LS=((X1,Y1,Z1)-H(x1,y1,z1))+((X2,Y2,Z2)-H(x2,y2,z2))+((X3,Y3,Z3)-H(x3,y3,z3))$$

The position comparing function 37b can convert a scan range that is specified on the virtual patient image into a scan range on the positioning image, by the acquired coordinate transformation matrix "H". For example, the position comparing function 37b can convert a scan range "SRV" specified on the virtual patient image into a scan range "SRC" on the positioning image as shown in FIG. 8, by using the coordinate transformation matrix "H". FIG. 9 shows a conversion example of a scan range by coordinate transformation according to the first embodiment. For example, as shown on the virtual patient image in FIG. 9, when an operator sets the scan range "SRV" on the virtual patient image, the position comparing function 37b converts the set scan range "SRV" into the scan range "SRC" on the scano-image by using the coordinate transformation matrix described above.

Thus, for example, the scan range "SRV" set to include a landmark corresponding to an identification code "Vn" on the virtual patient image is converted into the scan range including an identification code "Cn" corresponding to the same landmark on the scano-image to be set. The coordinate transformation matrix "H" can be stored in the storage 35 per subject and read to be used as necessary, or can be calculated each time a scano-image is collected. As described, according to the first embodiment, by displaying a virtual patient image for a range specification at preset and by planning a position/range thereon, numerical values can be set automatically for a position/range on a positioning image corresponding to the planned position/range after a positioning image (scano-image) is imaged.

Referring back to FIG. 2, the processing circuitry 37 includes the storing function 37c and the updating function 37d, and performs a control to improve the reproducibility in imaging. The control is described in detail later.

Conventionally, even with the same imaging plan, there is a case in which the reproducibility in imaging cannot be guaranteed as operations can vary depending on an operator. For example, in scan range (imaging range) setting, preset (initially displayed information) of a scan range that is displayed on a positioning image is adjusted by operators by themselves. Therefore, due to differences in operation among the operators, imaging is performed in scan ranges in different sizes. As a result, even with the same imaging plan, the reproducibility in imaging cannot be maintained.

Therefore, the X-ray CT apparatus 1 according to the first embodiment has a configuration as explained below to improve the reproducibility in imaging. Although a case of improving the reproducibility relating to a scan range is exemplified in the following explanation, embodiments are not limited thereto. For example, also in settings of an imaging condition other than a scan range, the present embodiment is applicable when the reproducibility in imaging cannot be maintained due to differences in operation among operators.

The storage 35 stores, for example, a scan range. For example, the storage 35 stores a scan range per imaging plan.

FIG. 10 shows one example of information of a scan range per imaging plan that is stored in the storage 35 according to the first embodiment. As shown in FIG. 10, the storage 35 stores information in which an imaging plan, an imaging part, a scan start position, and a scan end position are associated with each other. Among these, the imaging plan is a list of imaging plans that have been registered in the X-ray CT apparatus 1. Moreover, the imaging part is information indicating a part of a subject, such as a lung, a large intestine, and a head, to be a subject of imaging in an imaging plan. Furthermore, the scan start position indicates a position at which scan is started, and the scan end position indicates a position at which the scan is ended. That is, a range between the scan start position and the scan end position corresponds to a scan range. The information about a scan range stored in the storage 35 is, for example, registered in advance by an operator.

As shown in FIG. 10, for example, the storage 35 stores information in which an imaging plan "detailed examination of lung area", an imaging part "lung", a scan start position "1 cm above flag point (landmark) at upper end of right lung", and a scan end position "1 cm below flag point at lower end of left lung" are associated with each other. This information indicates that the imaging part in the imaging plan named "detailed examination of lung area" is a lung, and an area from 1 cm above a flag point (landmark) at an upper end of a right lung to 1 cm below a flag point at a lower end of a left lung is the scan area. Moreover, the storage 35 stores information about a scan range of other imaging plans similarly.

The storing function 37c accepts an operation indicating that an imaging condition is to be changed from an operator, and stores a history of accepted operations in the storage 35. For example, when accepting an operation indicating that a scan range as an imaging condition is to be changed from an operator, the storing function 37c stores a history of an accepted operation in the storage 35.

Figures 12, 13:
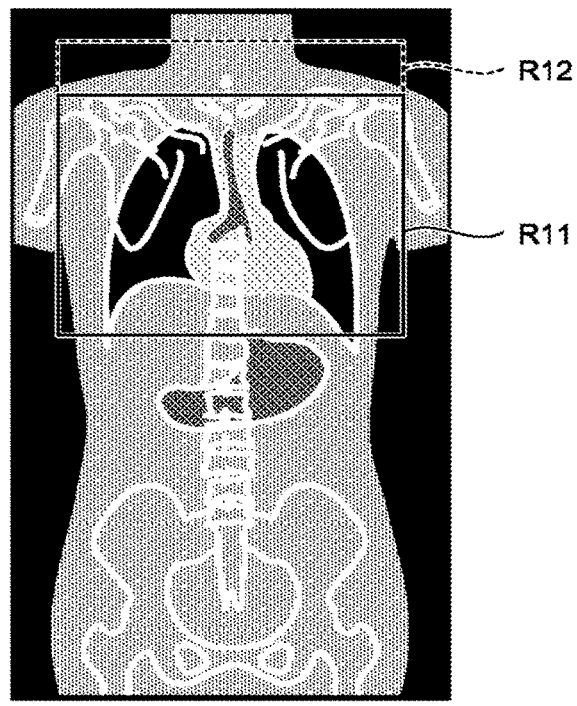
FIG. 12 is a diagram for explaining processing of the storing function according to the first embodiment.
FIG. 13 is a diagram for explaining processing of the storing function according to the first embodiment.

FIG. 11 to FIG. 13 are diagrams for explaining processing of the storing function 37c according to the first embodiment. In FIG. 11, a scan range R11 that is displayed on a positioning image is shown. In FIG. 12, a scan range R12 obtained after a change is made by an operator is shown. In FIG. 13, one example of the history of operations stored by the storing function 37c. In FIG. 11 to FIG. 13, a case in which "detailed examination of lung area" is selected as the imaging plan is explained.

As shown in FIG. 11, for example, when a scan range is set on a positioning image, the processing circuitry 37 acquires information about a scan range from the storage 35. Specifically, the processing circuitry 37 acquires the scan start position "1 cm above flag point (landmark) at upper end of right lung", and the scan end position "1 cm below flag point at lower end of left lung" from the storage 35 as the scan range corresponding to the imaging plan "detailed examination of lung area". The processing circuitry 37 then displays the scan range R11 that is indicated by the acquired scan start position "1 cm above flag point (landmark) at upper end of right lung" and scan end position "1 cm below flag point at lower end of left lung" on the positioning image (preset). Subsequently, the operator performs an operation to change a position or a range (size) of the scan range R11 as necessary.

As shown in FIG. 12, for example, the operator makes an operation to expand the scan range R11 for 3 cm upward, to obtain the scan range R12 by using the input circuit 31. At this time, accepting this operation, the storing function 37c stores a history of the accepted operation in the storage 35.

As shown in FIG. 13, for example, the storing function 37c stores information in which a date, a patient identification (ID), and an operation are associated with each other in the storage 35 per imaging plan as a history of an operation. Among these, the date is information indicating a date and a time when the operation is performed. Moreover, the patient ID is identification information to identify a patient of a subject of imaging. Furthermore, the operation is information indicating a performed operation. Accepting the change shown in FIG. 12, for example, the storing function 37c stores information in which a date "4/3 14:25", a patient ID "0101", and an operation "scan start position is moved 3 cm upward" are associated with each other in the storage 35 per imaging plan "detailed examination of lung area". Similarly, the storing function 37c stores a history of an accepted operation each time an operation to change a scan range is accepted.

As described, when accepting an operation to change a scan range, the storing function 37c stores a history of an accepted operation. Note that although it is preferable that a distance for which a scan range is changed be measured by a distance on the virtual patient image as the height of a subject is not uniform, it is not limited thereto, and for example, it can be measured by an actual distance.

Although a case I which an operation made by an operator on a positioning image has been explained in the above explanation of the storing function 37c, embodiments are not limited thereto. For example, the storing function 37c can accept an operation by an operator on a virtual patient image. In other words, the storing function 37c functions as an accepting unit that accepts an operation indicating that information relating to a range of a part that is defined based on multiple anatomical landmarks is to be changed, on image data of a subject, or a virtual patient image.

The updating function 37d updates a position that defines an imaging condition based on a history of operation stored in the storage 35. For example, the updating function 37d acquires a history of operation from the storage 35, identifies landmarks positioned near an outer rim of a range subjected to modification, and updates the position that defines an outer rim of a scan range to a position of landmarks that are identified predetermined times or more, out of the identified landmarks.

FIG. 14 and FIG. 15 are diagrams for explaining processing of the updating function 37d according the first embodiment. FIG. 14 shows information of a scan range that has been updated by the updating function 37d. FIG. 15 shows a scan range R13 that is initially displayed when the imaging plan "detailed examination of lung area" is performed after update by the updating function 37d. In FIG. 14 and FIG. 15, processing performed when the updating function 37d acquires the history of operation shown in FIG. 13 is explained.

For example, the updating function 37d acquires the history of operation shown in FIG. 13 from the storage 35. Three histories of date "4/3 14:25", "4/5 12:21", and "4/5 17:05" are all histories of changing a scan range toward an upward direction. In this case, the updating function 37d determines to expand the scan range upward. The updating function 37d identifies a flag point that is positioned near an outer rim of the range after the change. When a flag point at a neck is identified near an upper edge after the change in these three histories, the updating function 37d updates the position that defines an upper edge of the scan range to the flag point at the neck. For example, the updating function 37d updates the scan start position of the imaging plan "detailed examination of lung area" from "1 cm above flag point at upper end of right lung" (FIG. 10) to "flag point at neck" (FIG. 14). By this update, when the imaging plan "detailed examination of lung area" is performed next time and after, the processing circuitry 37 displays the scan range R13 indicated by the scan start position "flag point at neck" and the scan end position "1 cm below flag point at lower end of left lung".

As described, the updating function 37d updates the information of a scan range based on the history of operation stored in the storage 35. In other words, the updating function 37d functions as a setting unit that performs first setting processing of changing a part of anatomical landmarks to define a range of a part, or second setting processing of setting, for a part of anatomical landmarks, a position departed therefrom by a predetermined length in a predetermined direction as an actual anatomical landmark, based on the information relating to the scan range.

The information of a scan range to be set by the updating function 37d can be set directly by a flag point (anatomical landmark), or can be set as a position departed from the positional (coordinate) information of a flag point by a predetermined distance. Furthermore, the information of a scan range to be set by the updating function 37d can be set relatively based on multiple flag points. In this case, the information of a scan range to be set by the updating function 37d is expressed, for example, as "intermediate position between the first flag point and the second flag point", "position dividing a distance between the first flag point and the second flag point at predetermined ratio", or the like.

Figure 16:
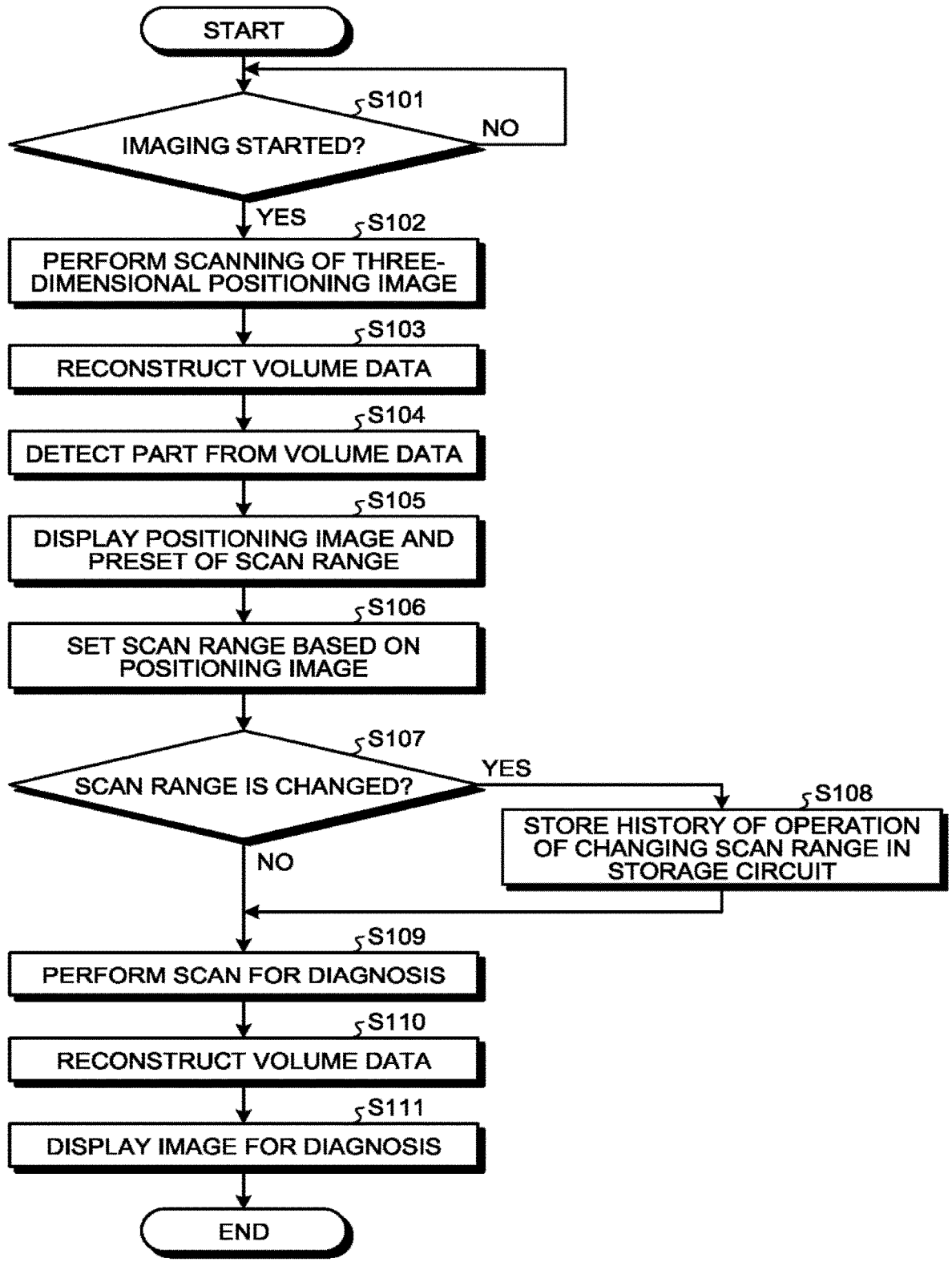
FIG. 16 is a flowchart showing a processing procedure by an X-ray CT apparatus according to the first embodiment.
Figure 17:
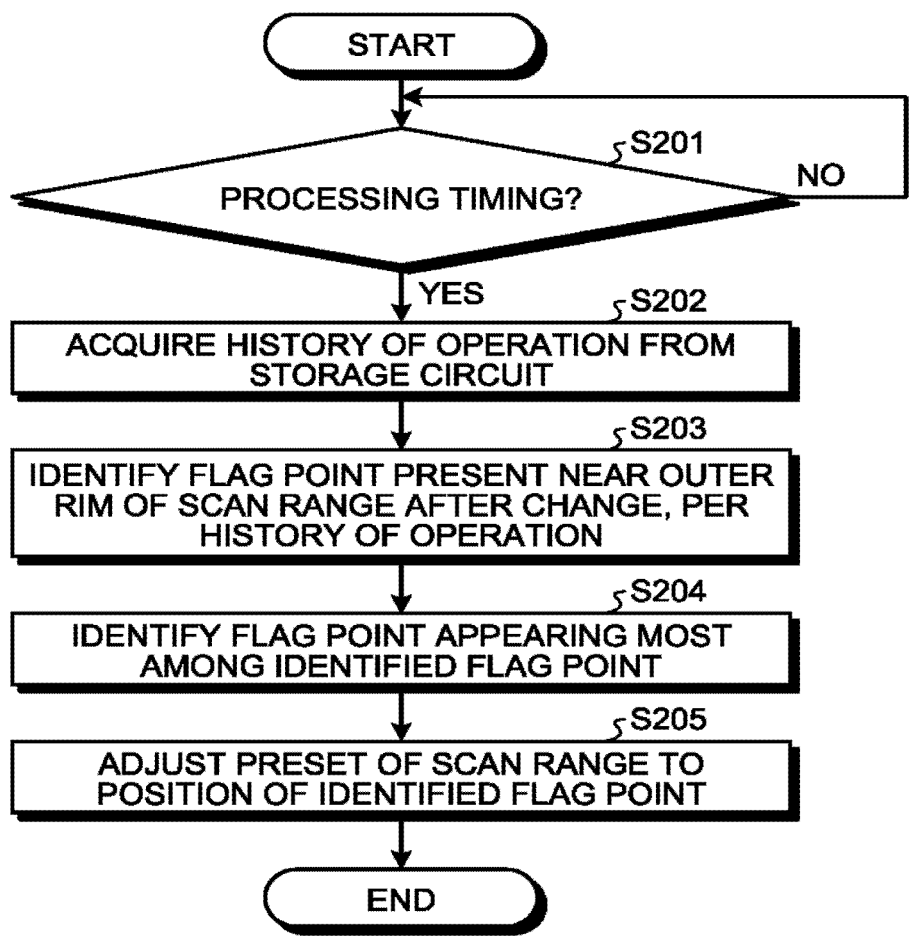
FIG. 17 is a flowchart showing processing procedure by the X-ray CT apparatus according to the first embodiment.

FIG. 16 and FIG. 17 are flowcharts showing a processing procedure by the X-ray CT apparatus 1 according to the first embodiment. In FIG. 16, processing when a history if an operation is stored by the storing function 37c in an examination is explained, and in FIG. 17, processing when a scan range is updated by the updating function 37d is explained.

Step S101 is a step corresponding to the scan control circuitry 33. Step S101 is a step at which the scan control circuitry 33 starts imaging. When step S101 is negative, the scan control circuitry 33 does not start imaging, and is in a standby state.

Step S102 is a step corresponding to the scan control circuitry 33. Step S102 is a step of performing three-dimensional scanning for a positioning image by the scan control circuitry 33 when step S101 is positive.

Step S103 is a step corresponding to the image reconstructing circuitry 36. Step S103 is a step of reconstructing volume data by the image reconstructing circuitry 36 from projection data collected by scanning for a positioning image.

Step S104 is a step corresponding to the detecting function 37a. It is a step of implementing the detecting function 37a by calling and executing a program of processing corresponding to the detecting function 37a from the storage 35 by the processing circuitry 37. Step S104 is a step of detecting multiple parts of a subject by the detecting function 37a, from the volume data that is obtained by reconstruction.

Step S105 is a step corresponding to the processing circuitry 37. Step S105 is a step of displaying a positioning image and a preset of a scan range by the processing circuitry 37 on the display 32.

Step S106 is a step corresponding to the input circuit 31. Step S106 is a step of accepting, by the input circuit 31, an operation to set (change) a scan range based on the positioning image.

Step S107 is a step corresponding to the storing function 37c. It is a step of implementing the storing function 37c by calling and executing a program corresponding to the storing function 37c from the storage 35 by the processing circuitry 37. Step S107 is a step of determining whether a scan range has been changed by the storing function 37c.

Step S108 is a step corresponding to the storing function 37c. It is a step of implementing the storing function 37c by calling and executing a program corresponding to processing of the storing function 37c from the storage 35 by the processing circuitry 37. Step S108 is a step of storing a history of operation changing a scan range in the storage 35 by the storing function 37c.

Step S109 is a step corresponding to the scan control circuitry 33. Step S109 is a step of performing scanning for diagnosis (actual scanning) by the scan control circuitry 33.

Step S110 is a step corresponding to the image reconstructing circuitry 36. Step S110 is a step of reconstructing volume data by the image reconstructing circuitry 36 from projection data collected by the actual scanning.

Step S111 is a step corresponding to the processing circuitry 37. Step S111 is a step of displaying an image for diagnosis based on the reconstructed volume data on the display 32 by the processing circuitry 37.

In FIG. 17, steps S201 to S205 are steps corresponding to the updating function 37d. It is a step of implementing the updating function 37d by calling and executing a program corresponding to processing of the updating function 37d from the storage 35 by the processing circuitry 37.

Step S201 is a step of determining whether it is processing timing by the updating function 37d. The processing timing can be arbitrary timing determined by an operator. For example, the updating function 37d determines that it is the processing timing when an instruction to start the processing to update a scan range is accepted from an operator. Moreover, for example, the updating function 37d determines the processing time periodically. Note that when step S201 is negative, the updating function 37d does not start the processing, and is in a standby state.

Step S202 is a step of acquiring a history of operation from the storage 35 by the updating function 37d when step S201 is positive.

Step S203 is a step of identifying a flag point positioned near an outer rim of a scan range subjected to a change by the updating function 37d per history of operation.

Step S204 is a step of identifying a flag point identified most, out of the identified flag points by the updating function 37d.

Step S205 is a step of adjusting a preset of a scan range to a position of the identified flag point by the updating function 37d.

Note that FIG. 16 and FIG. 17 are only one example. For example, the processing procedure above cannot be performed necessarily in the sequence described above. For example, steps S101 to S111 described above can be performed in a sequence modified appropriately within a range not causing a contradiction in the processing.

As described above, in the X-ray CT apparatus 1 according to the first embodiment, the storing function 37c accepts an operation indicating a scan range is to be changed from an operator, and stores a history of the accepted operation in the storage 35. The updating function 37d updates a position that defines the scan range based on the history of operation stored in the storage 35. Therefore, the X-ray CT apparatus 1 according to the first embodiment can improve the reproducibility in imaging.

For example, the X-ray CT apparatus 1 learns changes when a scan range stored per imaging plan is frequently changed, and reflects the changes to an initial display (preset) of a scan range next time and after. As described, as a scan range is updated to an appropriate size for each imaging plan, variations in operation among operators become less likely to be reflected in a scan range, and the reproducibility in imaging can be improved.

Moreover, generally, even though a scan range is determined per imaging part, the scan range is set relatively large or small depending on institutions. For example, in one institution, imaging is performed always including a neck when imaging a lung area. In this case, it has conventionally been necessary for an operator to change a scan range each time, and therefore, the reproducibility in imaging can be degraded due to differences in operation among operators. However, in the X-ray CT apparatus 1 according to the first embodiment, changes in a scan range are learned, and are reflected in an initial display of a scan range next time and after. Therefore, the position and the size of the scan range is gradually settled to a certain range, and the reproducibility in imaging can be improved.

Furthermore, generally, for example, operators tend to change a scan range using any kind of flag point (landmark) as a reference, as "let's take an image including a neck although it is a lung area imaging". In this point, as the X-ray CT apparatus 1 updates the initial display of a scan range by using landmarks of a part of the subject P, it is possible to change the scan range, reflecting an intention of changing by an operator.

Although a case of improving the reproducibility relating to a scan range has been explained in the above embodiment, embodiments are not limited thereto. For example, for a reconstruction range also, a history of operation indicating that a range is changed can be learned and reflected in next imaging and after, similarly. That is, the imaging condition that can be learned by the X-ray CT apparatus 1 is an imaging condition that is defined by at least one position of a part. Moreover, for example, an imaging condition such as a slice thickness can be learned also.

(Second Embodiment)

Although a case of updating a position of an outer rim of a scan range to that of a flag point has been explained in the above embodiment, embodiments are not limited thereto. For example, a position of an outer rim of a scan range can be updated by a distance changed by an operator.

The X-ray CT apparatus 1 according to a second embodiment has a configuration similar to that of the X-ray CT apparatus 1 shown in FIG. 2, and differs a part of processing performed by the updating function 37d. Therefore, in the second embodiment, a point that differs from the first embodiment is mainly explained, and explanation of a point of a function similar to the configuration explained in the first embodiment is omitted.

The updating function 37d acquires a history of operation from the storage 35, and identifies a landmark that is positioned near an outer rim of a range subjected to change, per acquired history of operation. When landmarks of all histories of operation are identified, the updating function 37d updates a position that defines the outer rim of the scan range to positions of landmarks that are identified predetermined times or more out of the identified landmarks. Moreover, when landmarks are not identified for all of the histories of operation, the updating function 37d updates a position that defines the outer rim of the scan range based on a minimum distance among changed distances.

Figure 18:
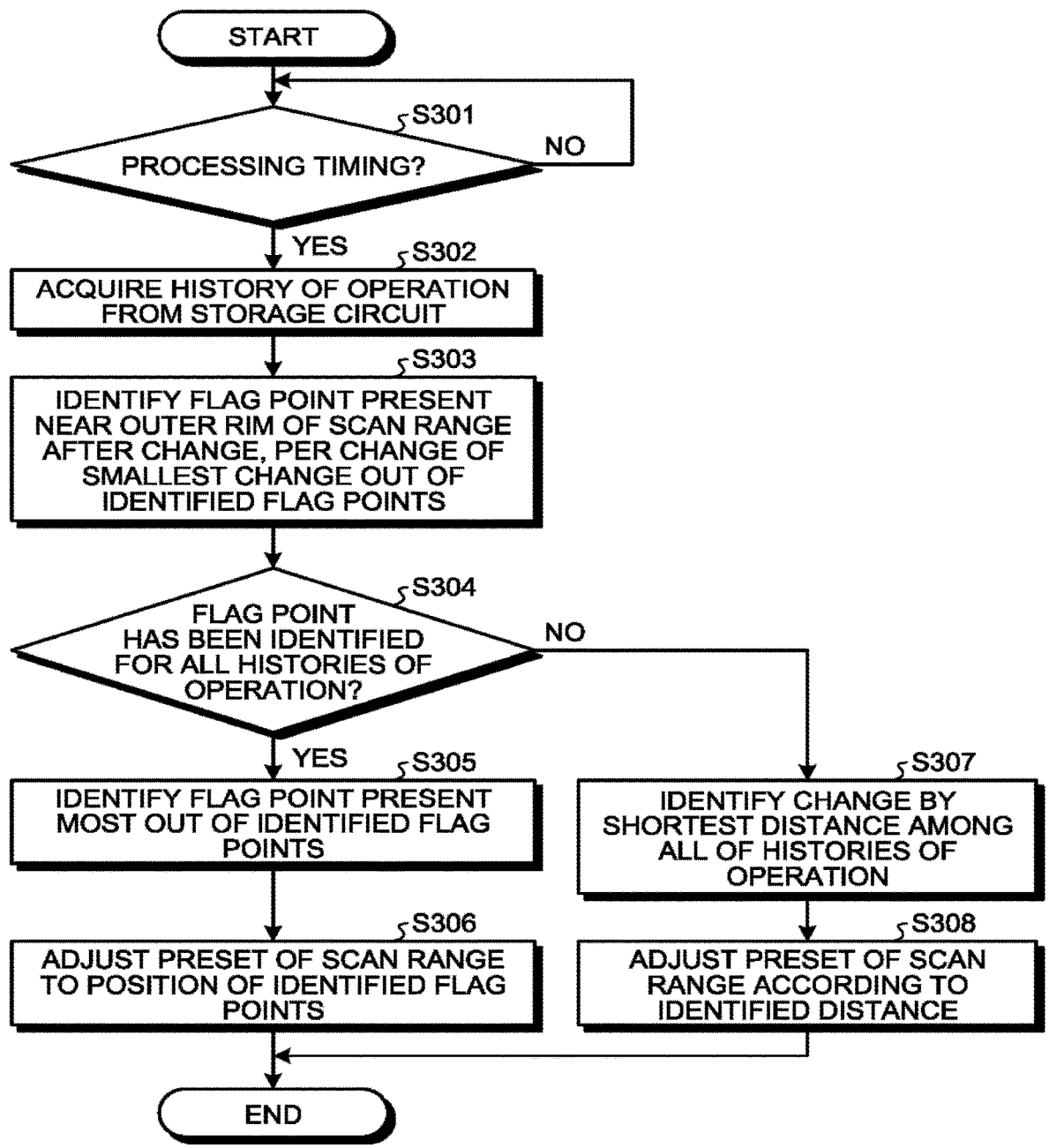
FIG. 18 is a flowchart showing a processing procedure by an X-ray CT apparatus according to a second embodiment.

FIG. 18 is a flowchart showing a processing procedure by the X-ray CT apparatus 1 according to the second embodiment. In FIG. 18, processing when a scan range is updated by the updating function 37d according to the second embodiment is explained.

In FIG. 18, steps S301 to S308 are steps corresponding to the updating function 37d according to the second embodiment. It is a step of implementing the updating function 37d by calling and executing a program corresponding to processing performed by the updating function 37d from the storage 35 by the processing circuitry 37. AS steps S301, S302, S305, and S306 are the same as steps S201, S202, S204, and S205 in FIG. 17, respectively, explanation thereof is omitted.

Step S303 is a step of identifying a flag point that is positioned near an outer rim of a scan range subjected to change per each shortest change out of histories of operation.

Step S304 is a step of determining whether a flag point has been determined for all of the histories of operations by the updating function 37d. For example, when three histories are acquired from the storage 35, the updating function 37d determines whether a flag point has been identified for all of the acquired three histories. When a flag point has been identified for all of the three histories, the updating function 37d shifts to step S305. On the other hand, when a flag point has not been identified for either one of the three histories, the updating function 37d shifts to step S307.

Step S307 is a step of identifying one for which a changed distance is the shortest among all of the histories of operation, by the updating function 37d. For example, when the change distances in the three histories are 3 cm, 4 cm, and 5 cm, the updating function 37d identifies the changed distance "3 cm".

Step S308 is a step of adjusting the preset of a scan range by the updating function 37d according to the identified distance. For example, the scan start position of a scan range of the imaging plan "detailed examination of lung area" in FIG. 10 is updated to a position 3 cm thereabove, the updating function 37d updates the scan start position "1 cm above flag point at upper end of right lung" to "4 cm above flag point at upper end of right lung" (see FIG. 19). FIG. 19 is a diagram for explaining the processing of the updating function 37d according to the second embodiment.

As described, if a flag point at an outer rim of a changed scan range is identified, the updating function 37d updates the position of the outer rim of the scan range to the flag point, and if a flag point is not identified, updates the position of the outer rim of the scan range based on a distance changed by the operator. Thus, even if an appropriate flag point is not present near a rim of a scan range, the scan range can be updated without fail.

Note that the example described above is only one example. For example, it can be arranged such that the updating function 37d does not perform update based on a flag point, and updates a position of an outer rim of a scan range based on a distance changed by an operator. Moreover, it is not necessarily limited to updating based on the shortest changed distance. For example, update can be performed using a mean value of changed distances.

(Third Embodiment)

Although a case in which imaging conditions that are defined by positions are learned has been explained in the above embodiment, relation between an examination order and an imaging plan can further be learned.

The X-ray CT apparatus 1 according to a third embodiment has a configuration similar to that of the X-ray CT apparatus 1 shown in FIG. 2, and a part of processing performed by the storing function 37c and the updating function 37d is different therefrom. Therefore, in the third embodiment, a point that differs from the first embodiment is mainly explained, and explanation of a point of a function similar to the configuration explained in the first embodiment is omitted.

The storing function 37c stores a history of selection in the storage 35 each time an imaging plan is selected according to an examination order. For example, when the X-ray CT apparatus 1 receives an examination order, the storing function 37c acquires what is included in the acquired examination order. Furthermore, when an imaging plan is selected as a plan of imaging of a patient included in this examination order, the storing function 37c stores the examination order and the imaging plan in the storage 35 in an associated manner.

FIG. 20 is a diagram for explaining processing by the storing function 37c according to the third embodiment. In FIG. 20, one example of histories of imaging plans selected according to examination orders is shown.

As shown in FIG. 20, for example, the storing function 37c stores information in which a date, a patient ID, an examination order, and an imaging plan are associated with each other in the storage 35 as a history. Among these, the date is information indicating a date and a time when the examination order is received. Furthermore, the examination order is information indicating keywords extracted from the examination order. For example, the storing function 37c stores information in which the date "4/3 14:25", the patient ID "0101", an examination order "colorectal cancer, detailed examination", and an imaging plan "detailed examination of colorectal cancer" are associated with each other in the storage 35.

The updating function 37d updates information of an imaging plan to be presented when an examination order is received, based on the examination order and the imaging plan included in the history stored in the storage 35.

For example, the updating function 37d extracts keywords from the history shown in FIG. 20 per imaging plan. Three histories of the dates "4/3 14:25", "4/5 12:21", and "4/5 17:05" are all histories of the imaging plan "detailed examination of colorectal cancer". The updating function 37d extracts a common keyword from the examination order of the three histories. In this case, "colorectal cancer" is extracted as a common keyword from the three histories. Therefore, if the keyword "colorectal cancer" is included in an examination order, the updating function 37d associates the keyword "colorectal cancer" and the imaging plan "detailed examination of colorectal cancer" to records/updates this information.

Thus, for example, the X-ray CT apparatus 1 extracts a keyword from a received examination order each time an examination order is received. Furthermore, if a keyword associated with an imaging plan is present among the extracted keywords, the X-ray CT apparatus 1 presents the imaging plan to the operator. According to this arrangement, the operator can select a desired imaging plan without searching for the desired imaging plan from multiple imaging plans. Moreover, in the imaging plan, the scan range has been set to an appropriate range. Therefore, the operator can perform imaging of a patient with less troubles.

Although a case in which one imaging plan is associated with a keyword of an examination order has been explained in the example in FIG. 20, more than one imaging plan can be associated therewith.

For example, the updating function 37d extracts "colorectal cancer" as a keyword that is included in an examination order with high frequency. The updating function 37d then searches for a history that includes the extracted keyword "colorectal cancer" in the examination order. When imaging plans "detailed examination of colorectal cancer" and "simple imaging of colorectal cancer" are extracted by this search, for example, the updating function 37d associates the two imaging plans "detailed examination of colorectal cancer" and "simple imaging of colorectal cancer" with the keyword "colorectal cancer". Thus, for example, when the keyword "colorectal cancer" is extracted from a received examination order, the X-ray CT apparatus 1 presents the two imaging plans "detailed examination of colorectal cancer" and "simple imaging of colorectal cancer" as candidates of an imaging plan, to an operator.

When multiple imaging plans are presented as candidates, the X-ray CT apparatus 1 can present them by assigning priority orders. In this case, for example, the X-ray CT apparatus 1 can present sequentially from an imaging plan included in histories with high frequency, or can present sequentially from an imaging plan with a latest date of record in histories (Other Embodiments)

Other than the embodiments described above, it can be implemented by various different forms.

(Unit of Learning)

Although a case in which an imaging condition is learned per imaging plan in an institution has been explained, embodiments are not limited thereto. For example, Learning can be performed in an arbitrary unit.

For example, when learning is performed per operator, the storage 35 stores information of a scan range per operator. Moreover, the storing function 37c stores a history of operation in the storage 35, accompanying identification information to identify an operator thereto. Furthermore, the updating function 37d updates the information of a scan range by using the identification information to identify an operator. Thus, the X-ray CT apparatus 1 is enabled to perform learning per operator.

(Sharing of Learning Results)

Moreover, although a case in which learning results (learned information) are held inside the X-ray CT apparatus 1 has been explained in the above embodiment, embodiments are not limited thereto. For example, learning results can be shared among different devices, and further, among institutions.

The storing function 37c acquires a history of operation that is stored in a device other than an own device. For example, the storing function 37c acquires, from another device inside or outside the institution connected by wired or wireless network, a history of operation that is recorded in the device. The storing function 37c then stores the acquired history of operation in the storage 35 of the own device. Not limited through network connection, the storing function 37c can acquire a history of operation by reading from, for example, a transportable storage medium in which the history of operation is recorded.

The storing function 37c updates a position that defines an imaging condition based on the history of operation of the own device or other devices stored in the storage 35. For example, even if it is a history of operation of the other device, a scan range is updated by using a history of a common imaging plan.

Information that can be shared is not limited to a history of operation. For example, the X-ray CT apparatus 1 can share information about a scan range updated by the updating function 37d with other devices inside or outside the institution.

(Changing of Settings of Preset)

Although a case in which histories of operation are collected and settings of an initial display (preset) of a scan range are updated by learning the collected histories of operation has been explained in the above embodiment, embodiments are not limited thereto.

For example, the storing function 37c displays a preset of a scan range on a positioning image or on a virtual patient image. The storing function 37c then accepts an operation to change the scan range on the positioning image or on the virtual patient image. In other words, the storing function 37c serving as an accepting unit accepts an operation indicating that information relating to a range of a part that is defined based on multiple anatomical landmarks in image data of a subject, or in image data of a virtual patient image.

Subsequently, the updating function 37d updates settings of a preset of a scan range based on the scan range that has been changed by an operator. That is, the updating function 37d updates the information about a scan range, for example, as explained in FIG. 14 and FIG. 15. In other words, based on information relating to the range of the part after the change, the updating function 37d serving as a setting unit performs the first setting processing of changing a part of anatomical landmarks to define the range of the part, or the second setting processing of setting, for a part of the anatomical landmarks, a position departed therefrom by a predetermined length in a predetermined direction as an actual anatomical landmark.

As described, the X-ray CT apparatus 1 can change settings of a preset of a scan range directly on a positioning image or on a virtual image.

(Application to Two-Dimensional Imaging)

Moreover, although a case in which positioning imaging and actual imaging are performed in a three-dimensional manner has been explained in the above embodiments, embodiments are not limited thereto. For example, the embodiments are applicable to a case in which positioning imaging and actual imaging are performed in a two-dimensional manner, and two-dimensional images (or positioning images) are collected.

(Medical Diagnostic Imaging Apparatus)

Furthermore, although a case in which the functions according to the embodiments are applied to the X-ray CT apparatus has been explained in the above embodiments, the embodiments are not limited thereto. For example, the function according to the embodiments described above can be applied to medical diagnostic imaging apparatuses, such as an X-ray diagnostic apparatus and an MRI apparatus, other than the X-ray CT apparatus 1.

For example, in the MRI apparatus, there is a case in which a scan range for next scanning is set on an image obtained by actual scanning (main scanning) in one sequence. In this case, the function (function corresponding to the storing function 37c) applied to the MRI apparatus can accept an operation to change a scan image on an image obtained by actual scanning.

(Medical-Information Management Apparatus)

Furthermore, although a case in which the functions according to the embodiments are provided in the X-ray CT apparatus 1 has been explained in the above embodiments, it is not limited thereto. For example, the detecting function 37a, the position comparing function 37b, the storing function 37c, and the updating function 37d shown in FIG. 2 can be provided in a medical-information management apparatus that is connected to the X-ray CT apparatus 1.

Figure 21:
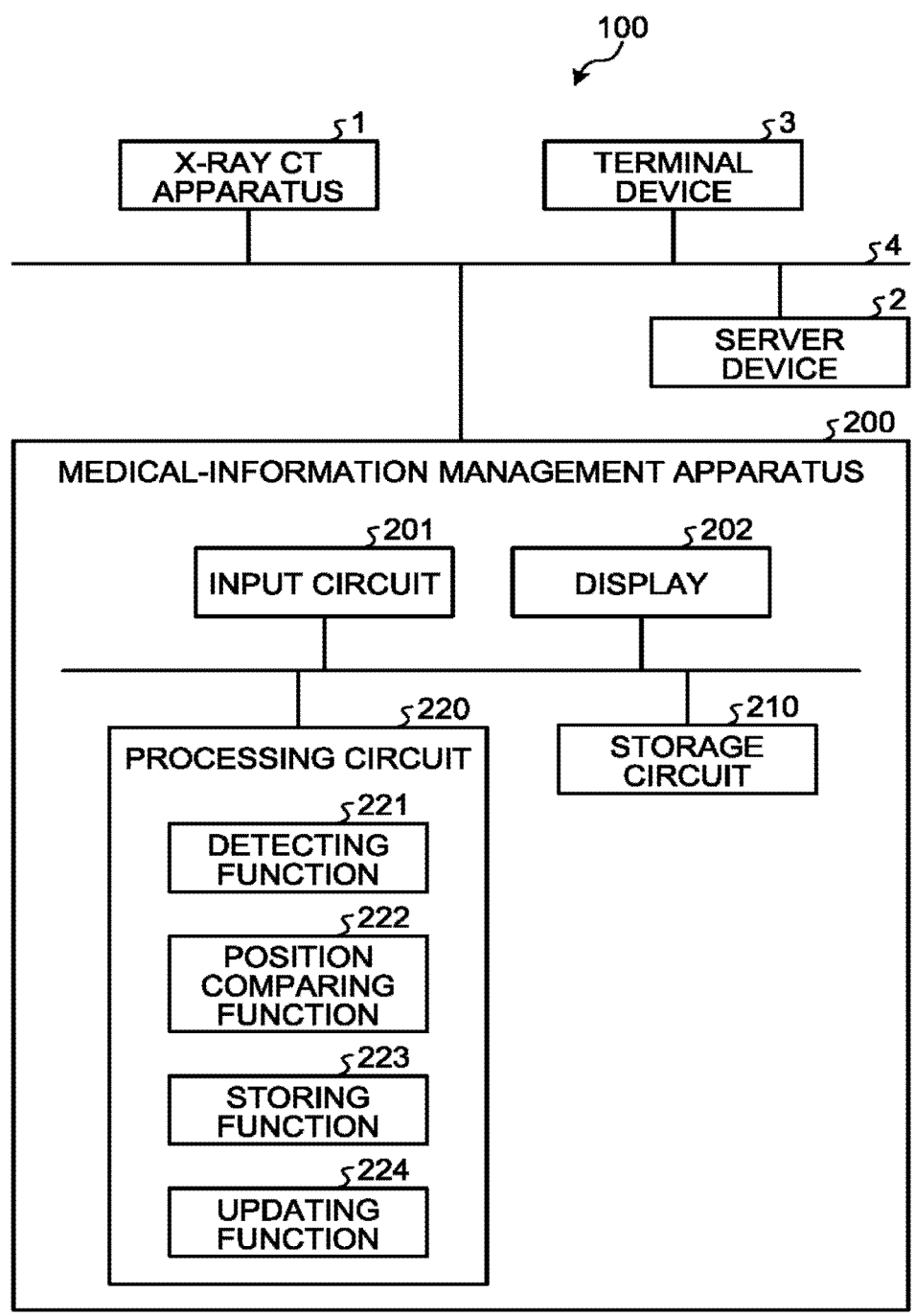
FIG. 21 shows one example of a configuration of a medical-information management apparatus according to another embodiment.

FIG. 21 shows one example of a configuration of a medical-information management apparatus according to another embodiment. FIG. 21 shows a case in which a medical-information management apparatus 200 is provided in the medical-information processing system 100 shown in FIG. 1.

The medical-information management apparatus 200 is a computer that performs condition setting and interpretation for imaging performed by medical diagnostic imaging apparatuses, such as the X-ray CT apparatus 1, an X-ray diagnostic apparatus, and an MRI apparatus. The medical-information management apparatus 200 shown in FIG. 21 controls the X-ray CT apparatus 1, thereby causing the X-ray CT apparatus 1 to perform positioning imaging and actual imaging. Furthermore, the medical-information management apparatus 200 can receive a history of operation collected by the X-ray CT apparatus 1 to display on a display 202, or can perform various kinds of processing. The medical-information management apparatus 200 can be provided in various institutions such as a hospital, or outside the institution.

As shown in FIG. 21, the medical-information management apparatus 200 includes an input circuit 201, the display 202, storage 210, and processing circuitry 220. As the input circuit 201, the display 202, and the storage 210 have configurations basically the same as those of the input circuit 31, the display 32, and the storage 35 shown in FIG. 2, explanation thereof is omitted.

The processing circuitry 220 is a processor that controls imaging performed by medical diagnostic imaging apparatuses. For example, the processing circuitry 220 controls CT scanning that is performed in the base 10, by controlling the scan control circuitry 33 of the X-ray CT apparatus 1. The processing circuitry 220 controls the image reconstruction processing and the image generation processing in the console 30, by controlling the image reconstructing circuitry 36 of the X-ray CT apparatus 1. The processing circuitry 220 controls the display 202 to display various kinds of image data stored in the storage 210.

Moreover, the processing circuitry 220 performs a detecting function 221, a position comparing function 222, a storing function 223, and an updating function 224 as shown in FIG. 21. For example, the detecting function 221, the position comparing function 222, the storing function 223, and the updating function 224 perform basically the same processing as that of the detecting function 37a, the position comparing function 37b, the storing function 37c, and the updating function 37d shown in FIG. 2.

That is, the storing function 223 serving as an accepting unit accepts an operation indicating that information relating to a range of a part that is defined based on anatomical landmarks is changed in image data of a subject or image data of a virtual patient image. The updating function 224 serving as a setting unit performs, based on information relating to a range of a part after change, the first setting processing of changing a part of anatomical landmarks to define a range of a part, or the second setting processing of setting, for a part of anatomical landmarks, a position departed therefrom by a predetermined length in a predetermined direction as an actual anatomical landmark. Thus, the medical-information management apparatus 200 can improve the reproducibility in imaging.

What is explained in FIG. 21 is only one example, and it is not limited to the illustrated example. For example, in the medical-information management apparatus 200, the storing function 223 stores, each time an imaging plan is selected according to an examination order, a history of selection in a predetermined storage unit. The updating function 224 updates information about an imaging plan to be presented when an examination order is received, based on the examination order and the imaging plan that are included in the history stored in the storage 210.

For example, the medical-information management apparatus 200 can include the preprocessing circuitry 34, and the image reconstructing circuitry 36 shown in FIG. 2. In this case, the medical-information management apparatus 200 receives projection data collected by positioning imaging, or projection data collected by actual imaging from the X-ray CT apparatus 1. The medical-information management apparatus 200 reconstructs a positioning image or an image for diagnosis from the received projection data.

Although it has been explained that the processing functions performed by the detecting function 37a, the position comparing function 37b, the storing function 37c, and the updating function 37d are implemented by a single unit of the processing circuitry 37 in FIG. 2, processing circuitry can be configured by combining multiple independent processors, and the functions can be implemented by executing programs by the respective processors.

The term "processor" used in the above explanation signifies a central processing unit (CPU), a graphics processing unit (GPU), or a circuit such as an application specific integrated circuit (ASIC), a programmable logic device (for example, a simple programmable logic device (SPLD), and a complex programmable logic device (CPLD)), and a field programmable gate array (FPGA). The processor implements the functions by reading and executing the program that are stored in storage. The programs can be configured to be directly installed in a circuit of the processor, instead of storing the programs in the storage. In this case, the processor implements the functions by reading and executing the program installed in the circuit. The respective processors of the present embodiment are not limited to be configured as a single circuit per processor, but can be configured as one processor by combining multiple independent circuits to implement the functions. Furthermore, the respective components in FIG. 2 can be combined to one processor, to implement the functions.

Furthermore, the respective components of the respective devices illustrated are of functional concept, and it is not necessarily required to be configured physically as illustrated. That is, specific forms of distribution and integration of the respective devices are not limited to the ones illustrated, and all or a part thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, all or a part of the processing explained as to be performed automatically out of the respective processing explained in the above embodiments can be performed manually also, while all or a part of the processing explained as to be performed manually can be performed automatically also by a publicly-known method. In addition, the processing procedures, the control procedures, the specific names and the information including various kinds of data and parameters indicated in the above document and drawings can be arbitrarily modified unless otherwise specified.

Furthermore, the imaging method explained in the above embodiments can be implemented by executing an imaging program that has been prepared in advance by a computer such as a personal computer and a workstation. This imaging method can be distributed through a network such as the Internet. Furthermore, this imaging method can be stored in a computer-readable recording medium, such as a hard disk, a flexible disk (FD), a compact-disc read-only memory (CD-ROM), a magneto optical disk (MO), and a digital versatile disc (DVD), and can be executed by being read by a computer from the recording medium.

According to at least one of the embodiments explained above, the reproducibility in imaging can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical diagnostic-imaging apparatus comprising processing circuitry configured to:
    accept an operation to change information relating to a scan range of an imaging part that is defined based on a plurality of anatomical landmarks in any one of image data of a subject and image data of a virtual patient image, and
    perform any one of a first setting processing and a second setting processing based on information relating to the scan range of the imaging part after the change, the first setting processing setting an anatomical landmark that is positioned near an outer rim of the scan range of the imaging part subjected to the change as an anatomical landmark to define the outer rim of the scan range of the imaging part, thereby changing a part of the plurality of anatomical landmarks to define the scan range of the imaging part, and the second setting processing setting, for a part of the plurality of anatomical landmarks, a position departed therefrom by a predetermined length in a predetermined direction as an actual anatomical landmark, wherein the processing circuitry is further configured to:
    reconstruct three-dimensional positioning image data from projection data that is collected by detecting an X-ray that has passed through the subject, in positioning imaging,
    detect a plurality of imaging parts of the subject included in the three-dimensional positioning image data,
    store a history of the operation in a predetermined storage, and
    perform any one of the first setting processing and the second setting processing, based on the history of the operation stored in the storage.

2. The medical diagnostic-imaging apparatus according to claim 1, wherein
    the processing circuitry acquires the history of the operation from the storage, identifies a landmark that is present near an outer rim of a scan range after change per the acquired history of the operation, and updates a position defining the outer rim of the scan range to a position of a landmark that is identified predetermined times or more out of the identified landmarks.

3. The medical diagnostic-imaging apparatus according to claim 2, wherein
    the processing circuitry stores a distance by which the scan range has been shifted on a virtual patient image, in the storage as the history.

4. The medical diagnostic-imaging apparatus according to claim 1, wherein
the processing circuitry acquires the history of the operation from the storage, identifies a distance by which a scan range after change has been shifted per the acquired history of the operation, and updates a position defining the outer rim of the scan range based on a shortest distance out of the identified distances.

5. The medical diagnostic-imaging apparatus according to claim 1, wherein
the processing circuitry acquires the history of the operation from the storage, identifies a landmark that is present near an outer rim of a scan range after change per the acquired history of the operation, and updates a position defining the outer rim of the scan range to a position of a landmark that is identified predetermined times or more out of the identified landmarks when the landmarks have been identified for all of histories of operation, and updates a position defining the outer rim of the scan range based on a shortest distance out of distances by which the change has been made when landmarks are not identified for all of the histories of operation.

6. The medical diagnostic-imaging apparatus according to claim 1, wherein
the processing circuitry further stores a history of selection in the storage each time an imaging plan is selected according to an examination order, and updates information about an imaging plan to be presented when the examination order is received, based on the examination order and the imaging plan that are included in the history stored in the storage.

7. The medical diagnostic-imaging apparatus according to claim 1, wherein
the processing circuitry acquires the history of the operation that is stored in other devices that are different from an own device, stores the acquired history of the operation in the storage of the own device, and performs any one of the first setting processing and the second setting processing based on the history of the operation of the own device and the other device stored in the storage.

8. A medical diagnostic-imaging apparatus comprising processing circuitry configured to:
receive an examination order from a device installed in a hospital,
select an imaging plan according to the examination order,
store, each time the imaging plan is selected, a history of selection in a predetermined storage, and
update information about an imaging plan to be presented when the examination order is received, based on the examination order and the imaging plan that are included in the history stored in the storage.

9. A medical-information management apparatus comprising processing circuitry configured to:
accept an operation to change information relating to a scan range of an imaging part that is defined based on a plurality of anatomical landmarks in any one of image data of a subject and image data of a virtual patient image, and
perform any one of a first setting processing and a second setting processing based on information relating to the scan range of the imaging part after the change, the first setting processing setting an anatomical landmark that is positioned near an outer rim of the scan range of the imaging part subjected to the change as an anatomical landmark to define the outer rim of the scan range of the imaging part, thereby changing a part of the plurality of anatomical landmarks to define the scan range of the imaging part, and the second setting processing setting, for a part of the plurality of anatomical landmarks, a position departed therefrom by a predetermined length in a predetermined direction as an actual anatomical landmark, wherein the processing circuitry is further configured to:
reconstruct three-dimensional positioning image data from projection data that is collected by detecting an X-ray that has passed through the subject, in positioning imaging,
detect a plurality of imaging parts of the subject included in the three-dimensional positioning image data,
store a history of the operation in a predetermined storage, and
perform any one of the first setting processing and the second setting processing, based on the history of the operation stored in the storage.

10. The medical-information management apparatus according to claim 9, wherein
the processing circuitry acquires the history of the operation from the storage, identifies a landmark that is present near an outer rim of a scan range after change per the acquired history of the operation, and updates a position defining the outer rim of the scan range to a position of a landmark that is identified predetermined times or more out of the identified landmarks.

11. The medical-information management apparatus according to claim 9, wherein
the processing circuitry acquires the history of the operation from the storage, identifies a distance by which a scan range after change has been shifted per the acquired history of the operation, and updates a position defining the outer rim of the scan range based on a shortest distance out of the identified distances.

12. The medical-information management apparatus according to claim 9, wherein
the processing circuitry acquires the history of the operation from the storage, identifies a landmark that is present near an outer rim of a scan range after change per the acquired history of the operation, and updates a position defining the outer rim of the scan range to a position of a landmark that is identified predetermined times or more out of the identified landmarks when the landmarks have been identified for all of histories of operation, and updates a position defining the outer rim of the scan range based on a shortest distance out of distances by which the change has been made when landmarks are not identified for all of the histories of operation.

13. The medical-information management apparatus according to claim 9, wherein
the processing circuitry further stores a history of selection in the storage each time an imaging plan is selected according to an examination order, and updates information about an imaging plan to be presented when the examination order is received, based on the examination order and the imaging plan that are included in the history stored in the storage.

14. A medical diagnostic-imaging apparatus comprising processing circuitry configured to:

reconstruct, in positioning imaging, three-dimensional positioning image data from projection data that is collected by detecting an X-ray that has passed through a subject;

detect a plurality of imaging parts of the subject included in the three-dimensional positioning image data;

accept an operation to change information relating to a scan range of an imaging part that is defined based on a plurality of anatomical landmarks in any one of image data of the subject and image data of a virtual patient image;

store a history of the operation in a predetermined storage; and perform any one of a first setting processing and a second setting processing based on the history of the operation stored in the storage, the first setting processing changing a part of the plurality of anatomical landmarks to define the scan range of the imaging part, and the second setting processing setting, for a part of the plurality of anatomical landmarks, a position departed therefrom by a predetermined length in a predetermined direction as an actual anatomical landmark.

15. The medical diagnostic-imaging apparatus according to claim 14, wherein the processing circuitry acquires the history of the operation from the storage, identifies a landmark that is present near an outer rim of a scan range after change per the acquired history of the operation, and updates a position defining the outer rim of the scan range to a position of a landmark that is identified predetermined times or more out of the identified landmarks.

16. The medical diagnostic-imaging apparatus according to claim 15, wherein the processing circuitry stores a distance by which the scan range has been shifted on a virtual patient image, in the storage as the history.

17. The medical diagnostic-imaging apparatus according to claim 14, wherein the processing circuitry acquires the history of the operation from the storage, identifies a distance by which a scan range after change has been shifted per the acquired history of the operation, and updates a position defining the outer rim of the scan range based on a shortest distance out of the identified distances.

18. The medical diagnostic-imaging apparatus according to claim 14, wherein the processing circuitry acquires the history of the operation from the storage, identifies a landmark that is present near an outer rim of a scan range after change per the acquired history of the operation, and updates a position defining the outer rim of the scan range to a position of a landmark that is identified predetermined times or more out of the identified landmarks when the landmarks have been identified for all of histories of operation, and updates a position defining the outer rim of the scan range based on a shortest distance out of distances by which the change has been made when landmarks are not identified for all of the histories of operation.

19. The medical diagnostic-imaging apparatus according to claim 14, wherein the processing circuitry further stores a history of selection in the storage each time an imaging plan is selected according to an examination order, and updates information about an imaging plan to be presented when the examination order is received, based on the examination order and the imaging plan that are included in the history stored in the storage.

20. The medical diagnostic-imaging apparatus according to claim 14, wherein the processing circuitry acquires the history of the operation that is stored in other devices that are different from an own device, stores the acquired history of the operation in the storage of the own device, and performs any one of the first setting processing and the second setting processing based on the history of the operation of the own device and the other device stored in the storage.

* * * * *